(12) United States Patent
Ahmed et al.

(10) Patent No.: US 11,219,644 B2
(45) Date of Patent: Jan. 11, 2022

(54) UNIVERSAL IMMUNE CELLS FOR CANCER IMMUNOTHERAPY

(71) Applicant: Baylor College of Medicine, Houston, TX (US)

(72) Inventors: Nabil M. Ahmed, Houston, TX (US); Kevin Bielamowicz, Houston, TX (US); Kristen Fousek, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 227 days.

(21) Appl. No.: 15/546,259

(22) PCT Filed: Jan. 26, 2016

(86) PCT No.: PCT/US2016/014951
§ 371 (c)(1),
(2) Date: Jul. 25, 2017

(87) PCT Pub. No.: WO2016/123122
PCT Pub. Date: Aug. 4, 2016

(65) Prior Publication Data
US 2018/0085399 A1   Mar. 29, 2018

Related U.S. Application Data

(60) Provisional application No. 62/107,804, filed on Jan. 26, 2015.

(51) Int. Cl.

| | |
|---|---|
| *A61K 35/17* | (2015.01) |
| *C07K 16/28* | (2006.01) |
| *C07K 16/32* | (2006.01) |
| *A61P 25/00* | (2006.01) |
| *A61K 48/00* | (2006.01) |
| *C07K 14/725* | (2006.01) |
| *C07K 14/705* | (2006.01) |
| *G01N 33/574* | (2006.01) |
| *A61K 35/00* | (2006.01) |
| *A61K 39/00* | (2006.01) |
| *A61K 35/12* | (2015.01) |
| *C12N 15/86* | (2006.01) |

(52) U.S. Cl.
CPC .......... *A61K 35/17* (2013.01); *A61K 48/005* (2013.01); *A61P 25/00* (2018.01); *C07K 14/7051* (2013.01); *C07K 14/70521* (2013.01); *C07K 14/70578* (2013.01); *C07K 16/2866* (2013.01); *C07K 16/32* (2013.01); *G01N 33/574* (2013.01); *A61K 35/00* (2013.01); *A61K 2035/124* (2013.01); *A61K 2039/505* (2013.01); *C07K 2317/73* (2013.01); *C07K 2319/00* (2013.01); *C07K 2319/02* (2013.01); *C07K 2319/03* (2013.01); *C12N 15/86* (2013.01); *C12N 2740/10043* (2013.01)

(58) Field of Classification Search
None
See application file for complete search history.

(56) References Cited

U.S. PATENT DOCUMENTS

| | | | | |
|---|---|---|---|---|
| 2008/0044413 | A1* | 2/2008 | Hammond | A61P 13/12 424/135.1 |
| 2012/0134970 | A1* | 5/2012 | Yang | C07K 16/40 424/93.21 |
| 2012/0148552 | A1* | 6/2012 | Jensen | C07K 14/7155 424/93.71 |
| 2013/0280220 | A1 | 10/2013 | Ahmed et al. | |
| 2014/0255363 | A1 | 9/2014 | Metelitsa et al. | |

FOREIGN PATENT DOCUMENTS

| | | |
|---|---|---|
| WO | 2014124143 A1 | 8/2014 |
| WO | 2014164544 A1 | 10/2014 |

OTHER PUBLICATIONS

Sun et al. Construction and Evaluation of a Novel Humanized HER2-speicific Chimeric Receptor. Breast Cancer Research, 2014. 16:R61, 10 pages.*
Hegde et al. "Combinational Targeting Offsets Antigen Escape and Enhances Effector Functions of Adoptively Transferred T Cells in Glioblastoma", Molecular Therapy, Nov. 1, 2013 (Nov. 1, 2013), vol. 21, No. 11, pp. 2087-2101, Nature Publishing Group, GB.
Krebs et al. "T cells redirected to IL13R[alpha]2 with IL13 mutein-CARs have antiglioma activity but also recognize IL13R[alpha]I", Cytotherapy, Aug. 1, 2014 (Aug. 1, 2014), vol. 16, No. 8, pp. 1121-1131.
Chow et al., "T Cells Redirected to EphA2 for the Immunotherapy of Glioblastoma", Molecular Therapy, Oct. 16, 2012 (Oct. 16, 2012), vol. 21, No. 3, pp. 629-637.
Grada et al., "TanCAR: A Novel Bispecific Chimeric Antigen Receptor for Cancer Immunotherapy", Molecular Therapy—Nucleic Acids, Jan. 1, 2013 (Jan. 1, 2013), vol. 2, e105, pp. 1-11.
Bielamowicz et al., "HG-108 Multispecific Chimeric Antigen Receptor (CAR) T-Cells Overcome Inter-Patient Tumor Heterogeneity and Exhibit Enhanded Anitiumor Functionality in the Treatment of Gliobastoma", Neuro-Oncology, Jun. 1, 2016 (Jun. 1, 2016), vol. 18, No. suppl 3, pp. iii73.3-iii73.
Ahmed et al., "HER2-Specific T Cells Target Primary Glioblastoma Stem Cells and Induce Regression of Autologous Experimental Tumors", Clinical Cancer Research, Jan. 15, 2010 (Jan. 15, 2010), vol. 16, No. 2, pp. 474-485.

* cited by examiner

*Primary Examiner* — James D Schultz
*Assistant Examiner* — Kimberly A Aron
(74) *Attorney, Agent, or Firm* — Norton Rose Fulbright US LLP

(57) ABSTRACT

Embodiments of the disclosure encompass adoptive immunotherapy related to cells expressing multiple chimeric antigen receptors (CARs). In specific embodiments, T cells express a HER2-specific CAR, an IL13 Rα2-specific CAR, and an EphA2-specific CAR. In particular embodiments, the cells are utilized for cancer treatment, including for glioblastoma.

9 Claims, 21 Drawing Sheets

| | Optimum Bispecific Combination | 1 Antigen | 2 Antigens | 3 Antigens |
|---|---|---|---|---|
| PN 084 | E+I | 90.40% | 97.77% | 98.55% |
| PN 125 | E+H | 78.20% | 92.49% | 93.68% |
| PN 065 | H+E | 85.20% | 94.19% | 96.33% |
| PN 085 | I+H | 81.10% | 88.50% | 95.85% |
| PN 023 | E+H | 88.50% | 95.75% | 95.75% |
| PN 122 | H+E | 85.50% | 96.29% | 97.90% |

FIG. 3

UNIVERSAL IMMUNE CELLS FOR CANCER IMMUNOTHERAPY

The present application is a national phase application under 35 U.S.C. § 371 that claims priority to International Application No. PCT/US2016/014951 filed Jul. 25, 2017, which claims priority to U.S. Provisional Application Ser. No. 62/107,804, filed on Jan. 26, 2015, both of which are incorporated by reference herein in their entirety.

TECHNICAL FIELD

Embodiments of the disclosure are directed at least to the fields of immunology, cell biology, molecular biology, and medicine, including cancer medicine.

BACKGROUND

Individuals with HER2-specific T-cells show killing of primary Glioblastoma (GBM) and induced regression of autologous orthotopic xenografts. Recent data from primary gliomas, other solid tumors, and leukemia indicate that there is a clear advantage for simultaneous co-targeting of a second antigen when specific antigens pairs that vary with each tumor are chosen.

Provided herein, therefore, are immune cells and constructs that serve to address a long-felt need in the art and to overcome deficiencies in the art related to adoptive transfer of therapeutic T-cells. In particular, a problem being solved by practices of the disclosure is one of escape variants, and the present disclosure addresses that need by providing CAR T cells that target multiple antigens expressed by a single tumor type.

BRIEF SUMMARY

The present invention is directed to methods and compositions related to cell therapy. In particular embodiments, the cell therapy is for an individual in need of cell therapy, such as a mammal, including a human. The cell therapy may be suitable for any medical condition, although in specific embodiments the cell therapy is for cancer. The cancer may be of any kind and of any stage. The individual may be of any age or either gender. In specific embodiments, the individual is known to have cancer, is at risk for having cancer, or is suspected of having cancer. The cancer may be a primary or metastatic cancer, and the cancer may be refractory to treatment. The individual may have had a relapse of the cancer. In specific embodiments, the cancer is glioblastoma but could be another solid tumor or tumor of the blood, such as leukemia.

In specific embodiments, the cancer is leukemia, lymphoma, myeloma, breast, lung, brain, colon, kidney, prostate, pancreatic, thyroid, bone, cervical, spleen, anal, esophageal, head and neck, stomach, gall bladder, melanoma, non-small cell lung cancer, and so forth, for example. In particular aspects, the cancer expresses two or more tumor antigens, and in specific embodiments the cell therapy targets the one or more tumor antigens. In particular embodiments, the cell therapy targets two or more, e.g., multiple, tumor antigens. In a more specific embodiment, the cell therapy targets the tumor antigens of HER2, IL13Rα2, EphA2, CD19, CD20, CD22, Baff, PSMA, MUC1, GPC2, CD56, GD2 and/or other tumor targets.

In particular embodiments of the invention, there are methods and compositions related to cells suitable for use in immunotherapy. In certain aspects, the methods and compositions of the invention are an improvement on techniques utilized in the art. In specific cases, embodiments of the invention are useful for improvements on cells utilized for immunotherapy of any kind, although in particular cases the immunotherapeutic cells are employed for cancer therapy. In particular embodiments, an individual is provided a therapeutic amount of cells of the disclosure, and the individual may be known to be in need of cancer treatment or suspected of being in need of cancer treatment. Methods of the disclosure may include steps of diagnosing, prognosticating, and/or typing a particular cancer.

In particular embodiments of the disclosure, one may employ universal immune cells that provide therapy to an individual in need, such as an individual with cancer. In specific embodiments, a universal immune cell is an immune cell that is able to recognize two or more tumor targets to enable the maximum elimination of cells in an individual tumor and to be universal to a large cohort of patients with the same type of tumor entity. The universality of an immune cell could thus vary with different types of tumors.

In certain aspects of the invention, the individual is provided with cells that provide therapy to the individual. The cells may be of any kind, but in specific embodiments the cells are capable of providing therapy to an individual having cancer cells that express one, two or all three of the HER2, IL13Rα2, and EphA2 tumor antigens or more antigens that include CD19, CD20, CD22, Baff, PSMA, MUC1, GPC2, CD56, GD2 or other tumor targets. In some cases the cancer cells are determined to express each of the HER2, IL13Rα2, and EphA2 tumor antigens. In certain embodiments, the presence of the HER2, IL13Rα2, and EphA2 tumor antigens on the cancer cells is not determined. The cells may be T cells. The cells, in specific embodiments, may be cytotoxic T lymphocytes (CTLs), NK cells, NKT cells, and so forth.

In one embodiment, provided herein is a method of treating cancer in an individual, comprising the step of delivering to the individual a therapeutically effective amount of a composition encompassed by the disclosure. In particular embodiments, provided herein is a method of treating cancer in an individual, comprising the step of delivering to the individual a therapeutically effective amount of any cells encompassed in the disclosure. In a specific embodiment, the individual has a cancer that expresses HER2, IL13Rα2, and EphA2. In specific embodiments, the cancer is glioblastoma.

In certain embodiments the cells may be T cells that are virus-specific. In specific embodiments, the virus may be EBV, CMV, Adenovirus, BK virus, HHV6, RSV, Influenza, Parainfluenza, Bocavirus, Coronavirus, LCMV, Mumps, Measles, Metapneumovirus, Parvovirus B, Rotavirus, West Nile Virus, JC, HHV7, SV40, or HIV, for example.

In embodiments of the invention, provided herein are methods and compositions related to therapeutic vectors and/or cells that harbor the vectors. In specific embodiments, the methods and compositions of the invention provide cells expressing two or more chimeric antigen receptors (CARs), each directed to a unique tumor antigen. In specific embodiments, said two or more CARs are directed to antigens expressed by the same tumor cell(s). In specific embodiments, the cells express CARs directed to two, or all three, of HER2, IL13Rα2, and EphA2. In another specific embodiment, provided herein are cells expressing two or more HER2, IL13Rα2, and EphA2-specific CARs whose expression is under the control of environment-specific regulation. In specific embodiments the environment is hypoxia. In some cases, the cells comprise a suicide gene in addition to or alternative to the environmental regulation.

In particular embodiments, immune cells of the disclosure in addition, or as an alternative, to targeting one or more of HER2, IL13Rα2, and/or EphA2 may target one or more other tumor antigens, and those one or more other tumor antigens may be targeted by a CAR, an engineered αβTCR, and/or a native receptor specific for HER2, IL13Rα2, or EphA2. Examples of other tumor antigens that may be targeted by the immune cells include BCMA, CSPG4, CD138, Melanoma-associated antigen (MAGE), Preferentially expressed antigen of melanoma (PRAME), survivin, CD19, CD20, CD22, k light chain, CD30, CD33, CD123, CD38, ROR1, ErbB2, ErbB3/4, ErbB dimers, EGFr vIII, carcinoembryonic antigen, EGP2, EGP40, mesothelin, TAG72, PSMA, NKG2D ligands, B7-H6, IL-13 receptor a2, MUC1, MUC16, CA9, GD2, GD3, HMW-MAA, CD171, Lewis Y, G250/CAIX, HLA-AI MAGE A1, HLA-A2 NY-ESO-1, PSCA, folate receptor-a, CD44v6, CD44v7/8, $a_vb_6$ integrin, 8H9, NCAM, VEGF receptors, 5T4, Baff, GPC2, CD56, Foetal AchR, NKG2D ligands, CD44v6, dual antigen, and universal. Any tumor antigen targeted by the cells of the disclosure may be on the surface of a cancer cell, inside the cancer cell, or in cells or stroma of the tumor microenvironment or within their cellular components. In certain embodiments, when an antigen in the tumor microenvironment is targeted, expression constructs for the entity targeting the tumor antigen (such as a CAR) may include hypoxia response regulatory elements, such that engineered T cells express the CAR (for example) at functional levels only within a hypoxic microenvironment, thereby limiting targeting of the antigen in other organs.

The CARs disclosed herein can be expressed in the cell from separate constructs, e.g., separate retroviral or lentiviral vectors. In certain embodiments, the CARs are expressed from a single vector as a single polycistronic construct, the product of which is, e.g., cleavable between CARs.

In some embodiments of the invention, there is an expression vector that encodes one, two, three, or more tumor antigen-specific CARs. In specific embodiments, the vector further comprises sequence that encodes an inducible suicide gene.

In particular embodiments, provided herein is a composition comprising: a) an expression construct that encodes a HER2-specific chimeric antigen receptor (CAR); b) an expression construct that encodes an IL13Rα2 CAR; and c) an expression construct that encodes an EphA2 CAR, wherein: 1) the expression construct of a) and b) and c) are located on separate molecules; 2) the expression construct of a) and b) are the located on same molecule; 3) the expression construct of a) and c) are located on the same molecule; 4) the expression construct of b) and c) are located on the same molecule; or 5) the expression construct of a), b), and c) are located on the same molecule. In specific embodiments, each of the expression constructs is comprised within one or more vectors. In a specific embodiment, the expression construct(s) of a), b), and/or c) are located on a single vector. In a specific embodiment, for the expression constructs of 2), 3), 4), or 5), the CARs of the expression constructs are expressable, or expressed, as a single open reading frame. In a particular embodiment, the expression vector further comprise sequence that encodes an inducible suicide gene. In specific embodiments, the suicide gene is selected from the group consisting of caspase 9, herpes simplex virus, thymidine kinase (HSV-tk), cytosine deaminase (CD) and cytochrome P450.

In certain embodiments, vectors of the disclosure may be a non-viral vector or a viral vector. In specific embodiments, the viral vector is a retroviral vector, lentiviral vector, adenoviral vector, or adeno-associated viral vector. In a particular embodiment, the CAR comprises an intracellular signaling domain selected from the group consisting of CD28, OX40, 4-1BB, ICOS and any combination thereof. In certain embodiments, one or more of the CARs comprises a transmembrane domain selected from the group consisting of CD3-zeta and CD28.

In embodiments of the disclosure there are cells comprising a composition encompassed in the disclosure. In a specific embodiment, the expression constructs of a), b), and c) are separate entities in the cell, and their gene products are separate entities in the cell. In specific embodiments, the cell is a eukaryotic cell, such as a human cell, including an immune cell. In specific embodiments, the cell is autologous, syngeneic, allogeneic, or xenogeneic in relation to a particular individual, e.g., a recipient of the cell. In specific embodiments, the individual is in need of cancer treatment, including in need of treatment for glioblastoma. The cells may be cytotoxic T lymphocytes (CTL), natural killer cells, or natural killer T cells. In a specific embodiment, the cell comprises at least one other CAR specific for an antigen other than HER2, IL13Rα2, or EphA2. The CAR may be specific for an antigen selected from the group consisting of Melanoma-associated antigen (MAGE), Preferentially expressed antigen of melanoma (PRAME), survivin, CD19, CD20, CD22, kappa light chain, lambda light chain, CD30, CD33, CD123, CD38, ROR1, ErbB2, ErbB3/4, ErbB dimers, EGFr vIII, carcinoembryonic antigen, EGP2, EGP40, mesothelin, TAG72, PSMA, NKG2D ligands, B7-H6, MUC1, MUC16, CA9, GD2, GD3, HMW-MAA, CD171, Lewis Y, Baff, GPC2, CD56, G250/CAIX, HLA-AI MAGE A1, HLA-A2 NY-ESO-1, PSCA, folate receptor-a, CD44v6, CD44v7/8, $a_vb_6$ integrin, 8H9, NCAM, VEGF receptors, 5T4, Foetal AchR, NKG2D ligands, CD44v6, dual antigen, and universal.

In certain embodiments provided herein are kits comprising any composition or cells encompassed in the disclosure.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

FIG. 3 shows examples from a variety of patients having immune cells with particular bispecific CAR combinations and the resultant killing percentages for target cancer cells having 1, 2, or 3 antigens.

DETAILED DESCRIPTION

Figure 1:
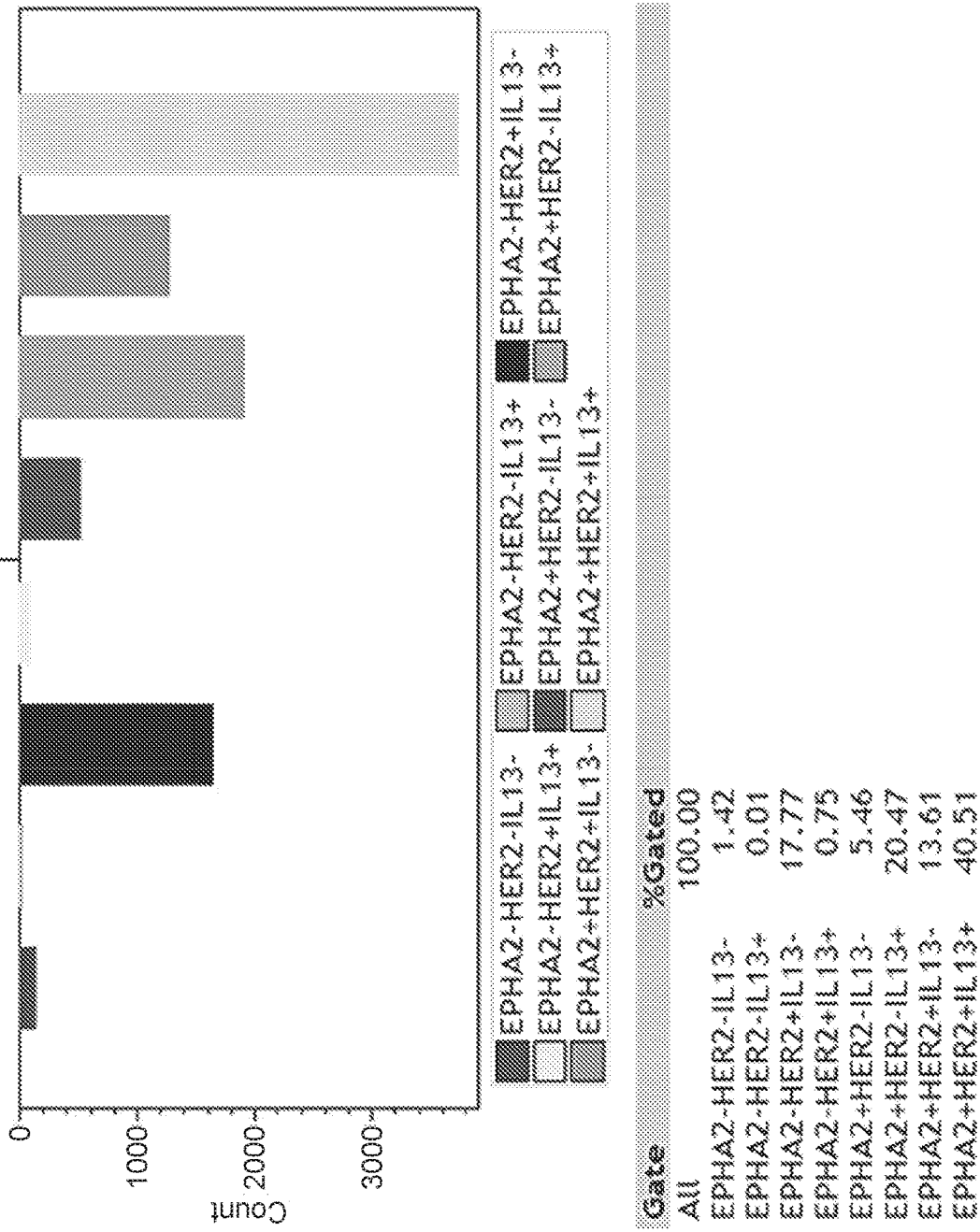
FIG. 1 demonstrates an antigen expression profile from one exemplary patient.

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%.

Reference throughout this specification to "one embodiment," "an embodiment," "a particular embodiment," "a related embodiment," "a certain embodiment," "an additional embodiment," "a further embodiment," "a certain aspect," a particular aspect," "a specific aspect," or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

I. General Embodiments of the Disclosure

Embodiments of the disclosure concern genetically modified cells (such as immune cells, including T cells, NK cells, NKT cells, and so forth) that target three different tumor antigens (for example, HER2, IL13rα2, and EphA2). In specific embodiments, the cells express one, two, three, or more different chimeric antigen receptors (CARs) that each target different antigens or that each employ a different scFv in the CAR. In specific cases, one transgene expresses multiple CAR molecules.

Embodiments of the disclosure concern immune cell products in which the immune cell is engineered to express a set of 2 or more chimeric antigen receptor molecules or similar recognition molecules (such as a bispecific antibody or others) or cells rendered multispecific using other engineering or non-engineering methodologies in a manner that targets the antigen expression pattern on a certain malignancy. The antigen expression pattern may be defined as prevalent antigen sets within single tumors or antigen sets prevalent across a cohort of tumors of a certain type. Thus, in specific embodiments the disclosure encompasses the use of one or more transgenes to express multiple CARs or similar molecules on immune cells. In other embodiments, the disclosure regards the use of immune cell-redirecting methodologies that assign two or more specificities to immune cells.

In embodiments of the invention, there are methods and compositions for treating cancers, such as glioblastoma, as an example. The methods and compositions are related to providing treatment that delivers therapy to certain tissues or cells in need but that avoids delivery to cells that are not in need. The methods and compositions are related to providing treatment that delivers therapy to cancerous tissues or cells expressing more than one tumor antigen but that avoids delivery to cells that do not express the more than one tumor antigens.

Embodiments of the disclosure encompass improvement of the specificity of immune cells comprising Chimeric Antigen Receptors (CARs). The engineered immune cells of the disclosure address the problem of cancers that recur upon targeting of a single tumor antigen, such as cancers that recur because of the emergence of an antigen-escape tumor cell population. Particular but exemplary cells directed to HER2 and described herein maintained positivity for two other validated glioma antigens, IL13Rα2 and EphA2, and in specific embodiments they serve as alternative targets to circumvent any escape mechanism.

Particular aspects of the invention provide therapy for glioblastoma (as an example) for an individual known to have glioblastoma, suspected of having glioblastoma, or at risk for developing glioblastoma. The individual may be determined to have glioblastoma by means other than identification of HER2/IL13Rα2 and/or EphA2-positive cancer cells, in some cases. In particular embodiments therapy for glioblastoma has already been provided or is being provided to the individual. The individual may be refractory to one or more glioblastoma therapies (other than that of the disclosure) of any kind initially or after some period of time on the therapy.

Embodiments of the invention include three chimeric antigen receptors that mediate trispecific activation and targeting of T cells. Given that single agents in cancer therapy fail to cure tumors while multiple agents achieve substantial responses (or cure), targeting multiple antigens using CAR T cells of the present disclosure results in (1) enhanced T cell activation, (2) effectively offsetting tumor escape by antigen loss, and (3) enhancing tumor control by capturing more tumor bulk and a collective action of the above former two effects. In certain embodiments, there is targeting of the tumor complex, wherein multi-specificity enables simultaneous targeting of tumor cells and elements in the tumor microenvironment.

In certain embodiments, immune cells of the disclosure (for example, T cells) are engineered to recognize one or more disease-specific B-cell antigens, such as CD22, CD20, ROR1, CD19, or a combination thereof.

In some embodiments, there is a method of killing cancer cells in an individual, comprising the step of providing to the individual a therapeutically effective amount of engineered cells of the invention.

II. Chimeric Antigen Receptors (CAR)

The present invention includes an artificial T cell receptor referred to as a CAR (it also may be called chimeric T cell receptors or chimeric immunoreceptors). In embodiments of the cells of the disclosure, a single CAR in the cell is specific for HER2, a single CAR in the cell is specific for IL13Rα2, and a single CAR in the cell is specific for EphA2, and the CARs for each of HER2, IL13Rα2, and EphA2 are separate entities. The separate CARs may or may not be transcribed from the same expression vector. Each of the CARs generally may include an ectodomain, transmembrane domain, and endodomain. Each of the CARs may be first generation, second generation, or third generation, in specific embodiments. In certain cases, one, two, or three CARs of the cells may be of a different generation of CAR than one or more other CARs of the same cell.

In general, an ectodomain of the CAR encompasses a signal peptide, antigen recognition domain, and a spacer that links the antigen recognition domain to the transmembrane domain. The antigen recognition domain generally will comprise a single chain variable fragment (scFv) specific for the respective HER2, IL13Rα2, and EphA2. However, in cases wherein there are CARs other than for HER2, IL13Rα2, and EphA2 in the same cell, the other CAR may comprise an scFv specific for any one of Melanoma-associated antigen (MAGE), Preferentially expressed antigen of melanoma (PRAME), survivin, CD19, CD20, CD22, k light chain, CD30, CD33, CD123, CD38, ROR1, ErbB2, ErbB3/4, EGFr vIII, carcinoembryonic antigen, EGP2, EGP40, mesothelin, TAG72, PSMA, NKG2D ligands, B7-H6, IL-13 receptor a2, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-a, CD44v6, CD44v7/8, 8H9, NCAM, VEGF receptors, 5T4, Fetal AchR, NKG2D ligands, or CD44v6, for example.

Examples of hinge regions for the ectodomain include the CH2CH3 region of immunoglobulin, the hinge region from IgG1, and portions of CD3. The transmembrane region may be of any kind, although in some cases it is CD28. The different CARs for HER2, IL13Rα2, and EphA2, respectively, may have the same or different transmembrane regions.

In general, the endodomain of the CAR of the disclosure is utilized for signal transmission in the cell after antigen recognition and cluster of the receptors. The most commonly used endodomain component is CD3-zeta that contains 3 ITAMs and which transmits an activation signal to the T cell after the antigen is bound. In some embodiments, additional co-stimulatory signaling is utilized, such as CD3-zeta in combination with CD28, 4-1BB, OX40, CD27, CD80, CD83, CD86, CD134, and/or CD137. In other specific embodiments, the domain is PD-1, PD-L1, CTLA4, or B7-H4. The different CARs for HER2, IL13Rα2, and EphA2, respectively, may have the same or different endodomains.

III. Suicide Genes

In embodiments of the disclosure, a suicide gene is employed in one or more particular expression vectors to permit the cell to kill itself through apoptosis at a desired point in time or location or physiological event, for example. The suicide gene may be present on the same expression vector as the HER2, IL13Rα2, and/or EphA2-CAR vector(s). Although suicide genes are known in the art and routinely used, in specific embodiments the suicide gene used in the invention is caspase 9, herpes simplex virus, thymidine kinase (HSV-tk), cytosine deaminase (CD) or cytochrome P450. In specific aspects the suicide gene is inducible and activated using a specific chemical inducer of dimerization (CID) (Ramos et al., 2010).

IV. Cells

Embodiments of cells of the invention include those that are capable of expressing one or more particular CARs and include T cells, NK cells, and NKT cells, for example. As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, a "host cell" can refer to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

In specific aspects, the cells are for adoptive transfer. The cells may be included in a pharmaceutical composition. The cells may be transformed or transfected with one or more vectors as described herein. The recombinant cells may be produced by introducing at least one of the vectors described herein. The presence of the vector in the cell mediates the expression of the appropriate receptor, and in some embodiments one or more constructs are integrated into the genome of the cell. That is, nucleic acid molecules or vectors that are introduced into the host may either integrate into the genome of the host or they may be maintained extrachromosomally.

In certain embodiments, it is contemplated that RNAs or proteinaceous sequences may be co expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for CAR-expressing RNAs, which could then be expressed in host cells transfected with the single vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

The cells used in the invention may be eukaryotic, including mammalian. The cells are particularly human, but can be associated with any animal of interest, particularly domesticated animals, such as equine, bovine, murine, ovine, canine, feline, etc. for use in their respective animal. Among these species, various types of cells can be involved, such as T cells, NK cells, NKT cells, etc. In specific embodiments, the cell further comprises a naturally occurring or engineered T cell receptor that targets HER2, IL13Rα2, or EphA2. In particular embodiments, the cell further comprises a naturally occurring or engineered T cell receptor that targets a tumor antigen that is not HER2, IL13Rα2, or EphA2.

The cells can be autologous cells, syngeneic cells, allogenic cells and even in some cases, xenogeneic cells. The cells may be modified by changing the major histocompatibility complex ("MHC") profile, by inactivating β2-microglobulin to prevent the formation of functional Class I MHC molecules, inactivation of Class II molecules, providing for expression of one or more MHC molecules, enhancing or inactivating cytotoxic capabilities by enhancing or inhibiting the expression of genes associated with the cytotoxic activity, or the like.

In some instances specific clones or oligoclonal cells may be of interest, where the cells have a particular specificity, such as T cells and B cells having a specific antigen specificity or homing target site specificity.

Cells of the invention having HER2-, IL13Rα2- and EphA2-specific CARs may also express additional CARs, may also express a natural or engineered αβTCR, and/or may be viral-specific, and any recombinant expression construct may be under the regulation of environmental, tissue-specific, or other regulatory elements.

In many situations one may wish to be able to kill the modified cells, where one wishes to terminate the treatment, the cells become neoplastic, in research where the absence of the cells after their presence is of interest, or other event. For this purpose one can provide for the expression of certain gene products in which one can kill the modified cells under controlled conditions. Suicide gene products, such as caspase 9, are examples of such products.

By way of illustration, cancer patients or patients susceptible to cancer or suspected of having cancer may be treated as follows. Cells modified as described herein may be administered to the patient and retained for extended periods of time. The individual may receive one or more administrations of the cells. Illustrative cells include HER2-, IL13Rα2- and EphA2-specific CARs T cells. The cell would be modified at least to express at least the HER2-, IL13Rα2- and EphA2-specific CARs and is provided to the individual in need thereof in sufficient quantities.

V. Therapeutic Uses of the Cells

In one embodiment, engineered immune cells are used for the prevention, treatment or amelioration of a cancerous disease, such as a tumorous disease. In particular embodiments, the pharmaceutical composition contemplated herein may be particularly useful in preventing, ameliorating and/or treating cancers (or ameliorating one or more symptoms thereof) in which having the multiple separately expressed CARs renders the cells of the pharmaceutical composition more effective than if the cells lacked expression of the CARs. In specific embodiments, cancer cells being treated with pharmaceutical compositions are effectively treated because cells of the pharmaceutical compositions have selective expression in a tumor microenvironment. In particular embodiments, the cancer is in the form of a solid tumor, such as a tumor having cancer cells that express HER2, IL13Rα2, and EphA2.

Provided herein is a method of treating a cancer in a patient, comprising administering to the patient a cell (e.g., a T cell) comprising two or more CARs that target an antigen characteristic of the cancer. In a specific embodiment, the cancer is glioma. In another specific embodiment, the cell comprises CARs that target two, or all, of HER2, EphA2, and Il13Ra2, for example.

As used herein "treatment" or "treating," includes any beneficial or desirable effect on the symptoms or pathology of a disease or pathological condition, and may include even minimal reductions in one or more measurable markers of the disease or condition being treated, e.g., cancer. Treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of the occurrence or recurrence of, a disease or condition, e.g., cancer. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

An individual may be subjected to compositions or methods of the disclosure that is at risk for a solid tumor. The individual may be at risk because of having one or more known risk factors, such as family or personal history, being a smoker, having one or more genetic markers, and so forth.

Possible indications for administration of the composition(s) of the immune cells are cancerous diseases, including tumorous diseases, including cancer of the breast, brain, bone, prostate, lung, colon, head and neck, skin, ovary, endometrium, cervix, kidney, lung, stomach, small intestine, liver, pancreas, testis, pituitary gland, blood, spleen, gall bladder, bile duct, esophagus, salivary glands and the thyroid gland, for example. In particular embodiments, the administration of the composition(s) of the disclosure is useful for all stages and types of cancer, including for minimal residual disease, early cancer, advanced cancer, and/or metastatic cancer and/or refractory cancer, for example.

The disclosure further encompasses co-administration protocols with other compounds that are effective against cancer. The clinical regimen for co-administration of the inventive cell(s) may encompass co-administration at the same time, before, or after the administration of the other component. Particular combination therapies include chemotherapy, radiation, surgery, hormone therapy, or other types of immunotherapy.

By way of illustration, cancer patients or patients susceptible to cancer or suspected of having cancer may be treated as follows. Engineered cells may be administered to the patient and retained for extended periods of time. The individual may receive one or more administrations of the cells. Illustrative cells include ex vivo expanded T-cells. In various embodiments, the cell is modified at least to express the bipartite or tripartite signaling receptors and is provided to the individual in need thereof in effective amount. In some embodiments, the cells may be injected directly into the tumor.

In some embodiments, the genetically modified cells are encapsulated to inhibit immune recognition and are placed at the site of the tumor. For example, the cells may be encapsulated in liposomes, alginate, or platelet-rich plasma.

In another embodiment, antigen-specific T cells may be modified to export hormones or factors that are exocytosed. By providing for enhanced exocytosis, a greater amount of the hormone or factor will be exported; in addition, if there is a feedback mechanism based on the amount of the hormone or factor in the cytoplasm, increased production of the hormone or factor will result. In one aspect, one may provide for induced expression of the hormone or factor, so that expression and export may be induced concomitantly.

Embodiments of the disclosure provide herein methods of determining antigens to target with a CAR of the present disclosure In particular embodiments, one can utilize combinatorial CAR-expressing cell (including T cell) products based on tumor antigen profiling to specifically target an individual patient's tumor. Thus, as part of a method of the disclosure or separate from a method of the disclosure, a sample from an individual may be analyzed for antigens that are expressed on cancer cells from the individual.

VI. Introduction of Constructs into Cells

The HER2-, IL13Rα2- and EphA2-specific CARs construct(s), or any constructs described herein, can be introduced as one or more DNA molecules or constructs, where there may be at least one marker that will allow for selection of host cells which contain the construct(s). The constructs can be prepared in conventional ways, where the genes and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagensis, etc., as appropriate. The construct(s) once completed and demonstrated to have the appropriate sequences may then be introduced into the host cell by any convenient means, including on one or more expression vectors. The constructs may be integrated and packaged into non-replicating, defective viral genomes like Adenovirus, Adeno-associated virus (AAV), or Herpes simplex virus (HSV) or others, including retroviral vectors, for infection or transduction into cells. The constructs may include viral sequences for transfection, if desired. Alternatively, the construct may be introduced by fusion, electroporation, biolistics, transfection, lipofection, or the like. The host cells may be grown and expanded in culture before introduction of the construct(s), followed by the appropriate treatment for introduction of the construct(s) and integration of the construct(s). The cells are then expanded and screened by virtue of a marker present in the construct. Various markers that may be used successfully include hprt, neomycin resistance, thymidine kinase, hygromycin resistance, etc.

In some instances, one may have a target site for homologous recombination, where it is desired that a construct be integrated at a particular locus. For example,) can knock-out an endogenous gene and replace it (at the same locus or elsewhere) with the gene encoded for by the construct using materials and methods as are known in the art for homologous recombination. For homologous recombination, one may use either .OMEGA. or O-vectors. See, for example, Thomas and Capecchi, Cell (1987) 51, 503-512; Mansour, et al., Nature (1988) 336, 348-352; and Joyner, et al., Nature (1989) 338, 153-156.

Vectors containing useful elements such as bacterial or yeast origins of replication, selectable and/or amplifiable markers, promoter/enhancer elements for expression in prokaryotes or eukaryotes, etc. that may be used to prepare stocks of construct DNAs and for carrying out transfections are well known in the art, and many are commercially available.

VII. Administration of Cells

The cells that have been modified with the DNA constructs are then grown in culture under selective conditions and cells that are selected as having the construct may then be expanded and further analyzed, using, for example; the polymerase chain reaction for determining the presence of the construct in the host cells. Once the modified host cells have been identified, they may then be used as planned, e.g., expanded in culture or introduced into a host organism.

Depending upon the nature of the cells, the cells may be introduced into a host organism, e.g., a mammal, in a wide variety of ways. The cells may be introduced at the site of the tumor, in specific embodiments, although in alternative embodiments the cells are provided systemically and hone to the cancer or are modified to hone to the cancer. The number of cells that are employed will depend upon a number of circumstances, the purpose for the introduction, the lifetime of the cells, the protocol to be used, for example, the number of administrations, the ability of the cells to multiply, the stability of the recombinant construct, and the like. The cells may be applied as a dispersion, generally being injected at or near the site of interest. The cells may be in a physiologically-acceptable medium.

The DNA introduction need not result in integration in every case. In some situations, transient maintenance of the DNA introduced may be sufficient. In this way, one could have a short term effect, where cells could be introduced into the host and then turned on after a predetermined time, for example, after the cells have been able to home to a particular site.

The cells may be administered as desired. Depending upon the response desired, the manner of administration, the life of the cells, the number of cells present, various protocols may be employed. The number of administrations will depend upon the factors described above at least in part.

It should be appreciated that the system is subject to many variables, such as the cellular response to the ligand, the efficiency of expression and, as appropriate, the level of secretion, the activity of the expression product, the particular need of the patient, which may vary with time and circumstances, the rate of loss of the cellular activity as a result of loss of cells or expression activity of individual cells, and the like. Therefore, it is expected that for each individual patient, even if there were universal cells which could be administered to the population at large, each patient would be monitored for the proper dosage for the individual, and such practices of monitoring a patient are routine in the art.

VIII. Pharmaceutical Compositions

The term "pharmaceutical composition" relates to a composition for administration to an individual and encompasses compositions of cells for immunotherapy. In specific embodiments, the cells for immunotherapy are engineered to express at least three CARs. In certain embodiments, the cells comprise one or more modifications in addition to the multiple CARs, such as one or more receptors, including artificial and natural receptors, for example receptors for tumor antigens. Particular receptors include an engineered αβTCR, although in some cases the cell comprises a native TCR. In certain embodiments, the composition comprises a CAR other than the CARs for HER2, IL13Rα2, and EphA2. In particular embodiments, the CAR comprises a costimulatory domain.

In a particular embodiment, the pharmaceutical composition comprises a composition for parenteral, transdermal, intraluminal, intra-arterial, intrathecal or intravenous administration or for direct injection into a cancer. In one embodiment, the pharmaceutical composition is administered to the individual via infusion or injection. Administration of the suitable compositions may be effected by different ways, e.g., by intravenous, subcutaneous, intraperitoneal, intramuscular, topical or intradermal administration.

The pharmaceutical composition may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, etc. Compositions comprising such carriers can be formulated by well-known conventional methods. These pharmaceutical compositions can be administered to the subject at a suitable dose.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently.

The compositions of the disclosure may be administered locally or systemically. Administration will generally be parenteral, e.g., intravenous; DNA may also be administered directly to the target site, e.g., by biolistic delivery to an internal or external target site or by catheter to a site in an artery. In a preferred embodiment, the pharmaceutical composition is administered subcutaneously and in an even more preferred embodiment intravenously. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the pharmaceutical composition of the present disclosure might comprise proteinaceous carriers, like, e.g., serum albumin or immunoglobulin, preferably of human origin. In certain embodiments, the pharmaceutical composition of the disclosure comprises, in addition to the CAR constructs or nucleic acid molecules or vectors encoding the same (as described in this disclosure), further biologically active agents, depending on the intended use of the pharmaceutical composition.

IX. Polynucleotides Encoding Signaling Molecules for Bipartite or Tripartite Immune Cells The present disclosure also encompasses a composition comprising one or more nucleic acid sequences encoding one or more CARs as defined herein and cells harboring the nucleic acid sequence(s). The nucleic acid molecule is a recombinant nucleic acid molecule, in particular embodiments. In particular embodiments, the nucleic acid molecule is synthetic. It may comprise DNA, RNA as well as PNA (peptide nucleic acid) and it may be a hybrid thereof.

It is evident to the person skilled in the art that one or more regulatory sequences may be added to the nucleic acid molecule comprised in the composition of the disclosure. For example, promoters, transcriptional enhancers and/or sequences that allow for induced expression of the polynucleotide of the disclosure may be employed. A suitable inducible system is for example tetracycline-regulated gene expression as described, e.g., by Gossen and Bujard (Proc. Natl. Acad. Sci. USA 89 (1992), 5547-5551) and Gossen et al. (Trends Biotech. 12 (1994), 58-62), or a dexamethasone-inducible gene expression system as described, e.g. by Crook (1989) EMBO J. 8, 513-519.

Furthermore, it is envisaged for further purposes that nucleic acid molecules may contain, for example, thioester bonds and/or nucleotide analogues. The modifications may be useful for the stabilization of the nucleic acid molecule against endo- and/or exonucleases in the cell. The nucleic acid molecules may be transcribed by an appropriate vector comprising a chimeric gene that allows for the transcription of said nucleic acid molecule in the cell. In this respect, it is also to be understood that such polynucleotides can be used for "gene targeting" or "gene therapeutic" approaches. In another embodiment the nucleic acid molecules are labeled. Methods for the detection of nucleic acids are well known in the art, e.g., Southern and Northern blotting, PCR or primer extension. This embodiment may be useful for screening methods for verifying successful introduction of the nucleic acid molecules described above during gene therapy approaches.

The nucleic acid molecule(s) may be a recombinantly produced chimeric nucleic acid molecule comprising any of the aforementioned nucleic acid molecules either alone or in combination. In specific aspects, the nucleic acid molecule is part of a vector.

The present disclosure therefore also relates to a composition comprising a vector comprising the nucleic acid molecule described in the present disclosure.

Many suitable vectors are known to those skilled in molecular biology, the choice of which would depend on the function desired and include plasmids, cosmids, viruses, bacteriophages and other vectors used conventionally in genetic engineering. Methods that are well known to those skilled in the art can be used to construct various plasmids and vectors; see, for example, the techniques described in Sambrook et al. (1989) and Ausubel, Current Protocols in Molecular Biology, Green Publishing Associates and Wiley Interscience, N.Y. (1989), (1994). Alternatively, the polynucleotides and vectors of the disclosure can be reconstituted into liposomes for delivery to target cells. A cloning vector may be used to isolate individual sequences of DNA. Relevant sequences can be transferred into expression vectors where expression of a particular polypeptide is required. Typical cloning vectors include pBluescript SK, pGEM, pUC9, pBR322 and pGBT9. Typical expression vectors include pTRE, pCAL-n-EK, pESP-1, pOP13CAT.

In specific embodiments, there is a vector that comprises a nucleic acid sequence that is a regulatory sequence operably linked to the nucleic acid sequence encoding one or more CAR constructs defined herein. Such regulatory sequences (control elements) are known to the artisan and may include a promoter, a splice cassette, translation initiation codon, translation and insertion site for introducing an insert into the vector. In specific embodiments, the nucleic acid molecule is operatively linked to said expression control sequences allowing expression in eukaryotic or prokaryotic cells.

It is envisaged that a vector is an expression vector comprising the nucleic acid molecule encoding a polypeptide contemplated herein. In specific aspects, the vector is a viral vector, such as a lentiviral vector. Lentiviral vectors are commercially available, including from Clontech (Mountain View, Calif.) or GeneCopoeia (Rockville, Md.), for example.

The terms "regulatory sequence" or "expression control sequence" refers to DNA sequences that are necessary to effect the expression of coding sequences to which they are ligated. The nature of such control sequences differs depending upon the host organism. In prokaryotes, control sequences generally include promoters, ribosomal binding sites, and terminators. In eukaryotes generally control sequences include promoters, terminators and, in some instances, enhancers, transactivators or transcription factors. The term "expression control sequence" is intended to include, at a minimum, all components the presence of which are necessary for expression, and may also include additional advantageous components.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, a double-stranded nucleic acid is preferably used.

Thus, the recited vector is an expression vector, in certain embodiments. An "expression vector" is a construct that can be used to transform a selected host and provides for expression of a coding sequence in the selected host. Expression vectors can for instance be cloning vectors, binary vectors or integrating vectors. Expression comprises transcription of the nucleic acid molecule preferably into a translatable mRNA. Regulatory elements ensuring expression in prokaryotes and/or eukaryotic cells are well known to those skilled in the art. In the case of eukaryotic cells they comprise normally promoters ensuring initiation of transcription and optionally poly-A signals ensuring termination of transcription and stabilization of the transcript. Possible regulatory elements permitting expression in prokaryotic host cells comprise, e.g., the $P_L$, lac, trp or tac promoter in *E. coli*, and examples of regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells.

Beside elements that are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the recited nucleic acid sequence and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including an N-terminal identification peptide imparting desired characteristics, e.g., stabilization or simplified purification of expressed recombinant product; see supra. In this context, suitable expression vectors are known in the art such as Okayama-Berg cDNA expression vector pcDV1 (Pharmacia), pEF-Neo, pCDM8, pRc/CMV, pcDNA1, pcDNA3 (Invitrogen), pEF-DHFR and pEF-ADA, (Raum et al. Cancer Immunol Immunother (2001) 50(3), 141-150) or pSPORT1 (GIBCO BRL).

In some embodiments, the expression control sequences are eukaryotic promoter systems in vectors capable of transforming of transfecting eukaryotic host cells, but control sequences for prokaryotic hosts may also be used. Once the vector has been incorporated into the appropriate host, the host is maintained under conditions suitable for high level expression of the nucleotide sequences, and as desired, the collection and purification of the polypeptide of the disclosure may follow.

Additional regulatory elements may include transcriptional as well as translational enhancers. In particular embodiments, vectors comprises a selectable and/or scorable marker. Selectable marker genes useful for the selection of transformed cells are well known to those skilled in the art and comprise, for example, antimetabolite resistance as the basis of selection for dhfr, which confers resistance to methotrexate (Reiss, Plant Physiol. (Life-Sci. Adv.) 13 (1994), 143-149); npt, which confers resistance to the aminoglycosides neomycin, kanamycin and paromycin (Herrera-Estrella, EMBO J. 2 (1983), 987-995) and hygro, which confers resistance to hygromycin (Marsh, Gene 32 (1984), 481-485). Additional selectable genes have been described, namely trpB, which allows cells to utilize indole in place of tryptophan; hisD, which allows cells to utilize histinol in place of histidine (Hartman, Proc. Natl. Acad. Sci. USA 85 (1988), 8047); mannose-6-phosphate isomerase which allows cells to utilize mannose (WO 94/20627) and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.) or deaminase from *Aspergillus terreus* which confers resistance to Blasticidin S (Tamura, Biosci. Biotechnol. Biochem. 59 (1995), 2336-2338).

Useful scorable markers are also known to those skilled in the art and are commercially available. Advantageously, said marker is a gene encoding luciferase (Giacomin, Pl. Sci. 116 (1996), 59-72; Scikantha, J. Bact. 178 (1996), 121), green fluorescent protein (Gerdes, FEBS Lett. 389 (1996), 44-47) or β-glucuronidase (Jefferson, EMBO J. 6 (1987), 3901-3907). This embodiment is particularly useful for simple and rapid screening of cells, tissues and organisms containing a recited vector.

As described above, the recited nucleic acid molecule can be used in a cell, alone, or as part of a vector to express the encoded polypeptide in cells. The nucleic acids or vectors containing the DNA sequence(s) encoding any one of the above described chimeric cytokine receptor constructs is introduced into the cells that in turn produce the polypeptide of interest. The recited nucleic acids and vectors may be designed for direct introduction or for introduction via liposomes, or viral vectors (e.g., adenoviral, retroviral) into a cell. In certain embodiments, the cells are T-cells, CAR T-cells, NK cells, NKT-cells, MSCs, neuronal stem cells, or hematopoietic stem cells, for example.

In accordance with the above, the present disclosure relates to methods to derive vectors, particularly plasmids, cosmids, viruses and bacteriophages used conventionally in genetic engineering that comprise a nucleic acid molecule encoding the polypeptide sequence of a chimeric cytokine receptor construct contemplated herein. In particular embodiments, the vector is an expression vector and/or a gene transfer or targeting vector. Expression vectors derived from viruses such as retroviruses, vaccinia virus, adeno-associated virus, herpes viruses, or bovine papilloma virus, may be used for delivery of the recited polynucleotides or vector into targeted cell populations. Methods which are well known to those skilled in the art can be used to construct recombinant vectors; see, for example, the techniques described in Sambrook et al. (loc cit.), Ausubel (1989, loc cit.) or other standard text books. Alternatively, the recited nucleic acid molecules and vectors can be reconstituted into liposomes for delivery to target cells. The vectors containing the nucleic acid molecules of the disclosure can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook, supra.

X. Nucleic Acid-Based Expression Systems

General embodiments of particular nucleic acid-based expression systems that may be utilized in aspects of the disclosure are described.

A. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

B. Promoters and Enhancers

Regulatory sequences employed in the invention include one or more elements that are functionally linked to the expression construct of which the expression is regulated. The following describes other regulatory elements that may be employed.

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize their activity, is well known to those of skill in the art.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

In certain embodiments of the invention, the use of internal ribosome entry sites (IRES) elements are used to create multigene, or polycistronic, messages, and these may be used in the invention.

Vectors can include a multiple cloning site (MCS), which is a nucleic acid region that contains multiple restriction enzyme sites, any of which can be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Splicing sites, termination signals, origins of replication, and selectable markers may also be employed.

C. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™ 11 may be utilized in making a recombinant phage vector which can be used to transform host cells, such as, for example, *E. coli* LE392.

Further useful plasmid vectors include pIN vectors (Inouye et al., 1985); and pGEX vectors, for use in generating glutathione S transferase (GST) soluble fusion proteins for later purification and separation or cleavage. Other suitable fusion proteins are those with ☐ galactosidase, ubiquitin, and the like.

Bacterial host cells, for example, *E. coli*, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

D. Viral Vectors

The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells). Components of the present invention may be a viral vector that encodes one or more of the CARs of the disclosure. Non-limiting examples of virus vectors that may be used to deliver a nucleic acid of the present invention are described below.

1. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell specific construct that has been cloned therein. Knowledge of the genetic organization or adenovirus, a 36 kb, linear, double stranded DNA virus, allows substitution of large pieces of adenoviral DNA with foreign sequences up to 7 kb (Grunhaus and Horwitz, 1992).

2. AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno associated virus (AAV) is an attractive vector system for use in the cells of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

3. Retroviral Vectors

Retroviruses are useful as delivery vectors because of their ability to integrate their genes into the host genome, transferring a large amount of foreign genetic material, infecting a broad spectrum of species and cell types and of being packaged in special cell lines (Miller, 1992).

In order to construct a retroviral vector, a nucleic acid (e.g., one encoding part or all of the gene product of interest) is inserted into the viral genome in the place of certain viral sequences to produce a virus that is replication defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

4. Other Viral Vectors

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

E. Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

F. Vector Delivery and Cell Transformation

Suitable methods for nucleic acid delivery for transfection or transformation of cells are known to one of ordinary skill in the art. Such methods include, but are not limited to, direct delivery of DNA such as by ex vivo transfection, by injection, and so forth. Through the application of techniques known in the art, cells may be stably or transiently transformed.

G. Ex Vivo Transformation

Methods for transfecting eukaryotic cells and tissues removed from an organism in an ex vivo setting are known to those of skill in the art. Thus, it is contemplated that cells or tissues may be removed and transfected ex vivo using nucleic acids encoding CARs of the present disclosure. In particular aspects, the transplanted cells or tissues may be placed into an organism. In preferred facets, a nucleic acid is expressed in the transplanted cells.

XI. Glioblastoma

Glioblastomas (GBM; also known as Grade IV Astrocytoma) are tumors that arise from astrocytes. These tumors are usually highly malignant because the cells are supported by a large network of blood vessels and reproduce quickly. They are usually located in the cerebral hemispheres of the brain, but can also be present in other parts of the brain and in the spinal cord.

Glioblastomas are usually comprised of a mixture of cell types and materials, such as cystic mineral, calcium deposits, blood vessels, or a mixed grade of cells. There are two types of glioblastomas: 1) primary, or de novo, which form and make their presence known quickly; it is the most common form and is very aggressive; 2) secondary, which have a slower growth history, yet are still very aggressive. Glioblastoma may also be classified as giant cell glioblastoma or gliosarcoma. In embodiments of the disclosure, any type of glioblastoma may be treated with cells of the disclosure.

Symptoms of glioblastomas, given that they can grow rapidly, may be related to increased pressure in the brain. These symptoms can include seizure, headache, nausea, vomiting, and drowsiness. Depending on the tumor's location, individuals can develop a variety of other symptoms, including weakness on one side of the body, memory and/or speech difficulties, and visual changes. Although common symptoms of the disease include seizure, nausea and vomiting, headache, memory loss, and hemiparesis, the single most prevalent symptom is a progressive memory, personality, or neurological deficit due to temporal and frontal lobe involvement. The kind of symptoms produced depends highly on the location of the tumor, more so than on its pathological properties. The tumor can start producing symptoms quickly, but occasionally is an asymptomatic condition until it reaches a considerable size. An individual treated with embodiments of the disclosure may be experiencing one or more symptoms as described herein.

In some embodiments, methods of the disclosure include diagnosing the glioblastoma. Definitive diagnosis of a suspected GBM may utilize CT scan or MRI, and may include a stereotactic biopsy or a craniotomy with tumor resection and pathologic confirmation. Imaging of tumor blood flow using perfusion MRI and measuring tumor metabolite concentration with MR spectroscopy may be utilized in the diagnosis of glioblastoma, such as by showing increased relative cerebral blood volume and increased choline peak respectively. Pathology is commonly utilized.

In some cases, steps for the individual are incurred to relieve pressure on the brain, and as much tumor as possible may be removed through surgery. Treatment methods of the disclosure may be provided to the individual before, during, and/or after another treatment, including surgery, radiation, chemotherapy (such as with temozolomide and/or XRT), protein therapeutics (such as with APG101), microRNA techniques, and/or immunotherapy other than that disclosed herein.

The glioblastoma may be determined to have one or more particular molecular biomarkers, and this determination may occur before and/or after the onset of the therapy of the disclosure and/or of another therapy. Molecular biomarkers include, for example, O(6)-methlyguanine-DNA-methyltransferase (MGMT) promoter and deoxyribonucleic acid (DNA) methylation, loss of heterozygosity (LOH) of chromosomes 1p and 19q, loss of heterozygosity 10q, isocitrate dehydrogenase (IDH) mutations, epidermal growth factor receptor (EGFR), epidermal growth factor, latrophilin, and 7 transmembrane domain-containing protein 1 on chromosome 1 (ELTD1), vascular endothelial growth factor (VEGF), tumor suppressor protein p53, phosphatase and tensin homolog (PTEN), p16INK4a gene, cytochrome c oxidase (CcO), phospholipid metabolites, telomerase messenger expression (hTERT mRNA), and so forth.

Glioblastoma has been related with the viruses SV40, HHV-6, and cytomegalovirus, and in specific embodiments, and the immune cells (such as T cells) of the present disclosure may be specific for one or more of SV40, HHV-6, and cytomegalovirus.

The glioblastoma may be characterized by being one of certain subtypes, depending on the expression of epidermal growth factor receptor (EGFR), TP53, PDGFRA, IDH1, NF1, or others in the P53, RB, or the PI3K/AKT pathways, methylation of MGMT, and so forth.

XII. Kits of the Invention

Any of the compositions described herein may be comprised in a kit. In a non-limiting example, one or more cells for use in cell therapy that expresses HER2-, IL13Rα2- and EphA2-specific CARs and/or the reagents to generate one or more cells for use in cell therapy that harbors recombinantly-expressed CARs may be comprised in a kit. Any kit components are provided in suitable container means. The kit may also comprise cells that have viral-specific T cell receptors, polynucleotides that express HER2-, IL13Rα2- and EphA2-specific CARs, polynucleotides that express one or more CARs specific for an antigen other than HER2, IL13Rα2, and EphA2, primers suitable for amplication of any of the foregoing sequences, buffers, enzymes, and/or salts and so forth, for example.

Some components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the components in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly useful. In some cases, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means. The kits may also comprise a second container means for containing a sterile, pharmaceutically acceptable buffer and/ or other diluent.

In particular embodiments of the invention, cells that are to be used for cell therapy are provided in a kit, and in some cases the cells are essentially the sole component of the kit. The kit may comprise instead of or in addition to reagents and materials to make the cell recombinant for HER2, IL13Rα2, and EphA2 CARs. In specific embodiments, the reagents and materials include primers for amplifying the CARs (or regions thereof), nucleotides, suitable buffers or buffer reagents, salt, and so forth, and in some cases the reagents include vectors and/or DNA that encodes certain gene products and/or regulatory elements therefor.

In particular embodiments, there are one or more apparatuses in the kit suitable for extracting one or more samples from an individual. The apparatus may be a syringe, scalpel, and so forth.

In some cases of the invention, the kit, in addition to cell therapy embodiments, also includes a second cancer therapy, such as chemotherapy, hormone therapy, and/or immunotherapy, for example. The kit(s) may be tailored to a particular cancer for an individual and comprise respective second cancer therapies for the individual.

XIII. Combination Therapy

In certain embodiments of the disclosure, methods of the present disclosure for clinical aspects are combined with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cancer cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

In embodiments of the invention, one or more of the following are provided to an individual with glioblastoma in addition to the therapeutic cells of the invention: surgery, radiation, chemotherapy, immunotherapy, protein therapy, and so forth.

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver, et al., 1992). In the context of the present invention, it is contemplated that cell therapy could be used similarly in conjunction with chemotherapeutic, radiotherapeutic, or immunotherapeutic intervention, for example.

Alternatively, the present inventive therapy may precede or follow the other agent treatment by intervals ranging from minutes to weeks. In embodiments where the other agent and present invention are applied separately to the individual, one would generally ensure that a significant period of time did not expire between the time of each delivery, such that the agent and inventive therapy would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, present invention is "A" and the secondary agent, such as radio- or chemotherapy, is "B":

| A/B/A | B/A/B | B/B/A | A/A/B | A/B/B | B/A/A |
|-------|-------|-------|-------|-------|-------|
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

It is expected that the treatment cycles would be repeated as necessary. It also is contemplated that various standard therapies, as well as surgical intervention, may be applied in combination with the inventive cell therapy.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Universal CAR T-Cells for the Treatment of Glioblastoma

Described herein is a universal multi-specific T-cell product for adoptive immunotherapy of GBM by targeting three validated glioma antigens simultaneously.

A universal product of T cells expressing HER2, IL13Rα2 and EphA2 CARs is utilized as a broad therapeutic offsetting antigen-escape in GBM with variable antigenic profiles. Further, because the magnitude of T-cell response is determined by the balance between the density of target antigen expression as well as the density of CAR expression on T-cells, in specific embodiments co-expression of multiple CARs further enhances T-cell activation and improves their antitumor efficacy.

Multiple CARs targeting different glioma antigens can be successfully and proportionately expressed on individual T cells using, for example, a tri-cistronic construct with a single open reading frame. These T cells show specificity for each of three glioma antigens in vitro.

One can evaluate different multi-CAR strategies using a platform of primary human GBM material in an autologous set-up, evaluating the effector functions of multi-specific T-cells co-expressing CARs for HER2, IL13Rα2 and EphA2 in comparison to the optimal bispecific and unispecific T-cells—both in vitro (namely: ability to offset antigen escape, activation, cytolytic capacity, cytokine release and proliferation) and in an in vivo autologous orthotopic glioma murine model.

In particular studies, primary patient high-grade glioma samples exhibited varied expression of the three target antigens, HER2, IL13Rα2 and EphA2. In order to render single patients' T cells tri-specific, the inventors designed a transgene incorporating three encoding regions for HER2, IL13Rα2 and EphA2 CARs separated by viral 2A sequences (viral 2A sequences allow production of multiple protein products from a single transgene) in a single cassette driven by a single promoter. A retroviral system was employed to stably integrate this transgene into the primary T cell genome. CAR-specific flow cytometry indicated proportionate stable expression of individual CAR molecules on the T cell surface. These T cells show distinct specificity for each of the three glioma antigens evidenced by activation, proliferation, and cytolytic function in immunoassays. Therefore, the heterogeneity of antigenic expression in glioblastoma and antigen escape justify targeting multiple glioma antigens simultaneously. The inventors have successfully generated and tested a multi-specific T cell product for adoptive transfer that offsets antigen escape and exhibits an enhanced anti-glioma efficacy.

Example 2

Antigen Expression in Patient GBM Samples

To further describe the expression of TAAs in GBM, one can analyze at least 30 patient samples by flow cytometry of >100,000 events looking for surface expression of Her2, IL13Rα2, and EphA2.

Figure 2:
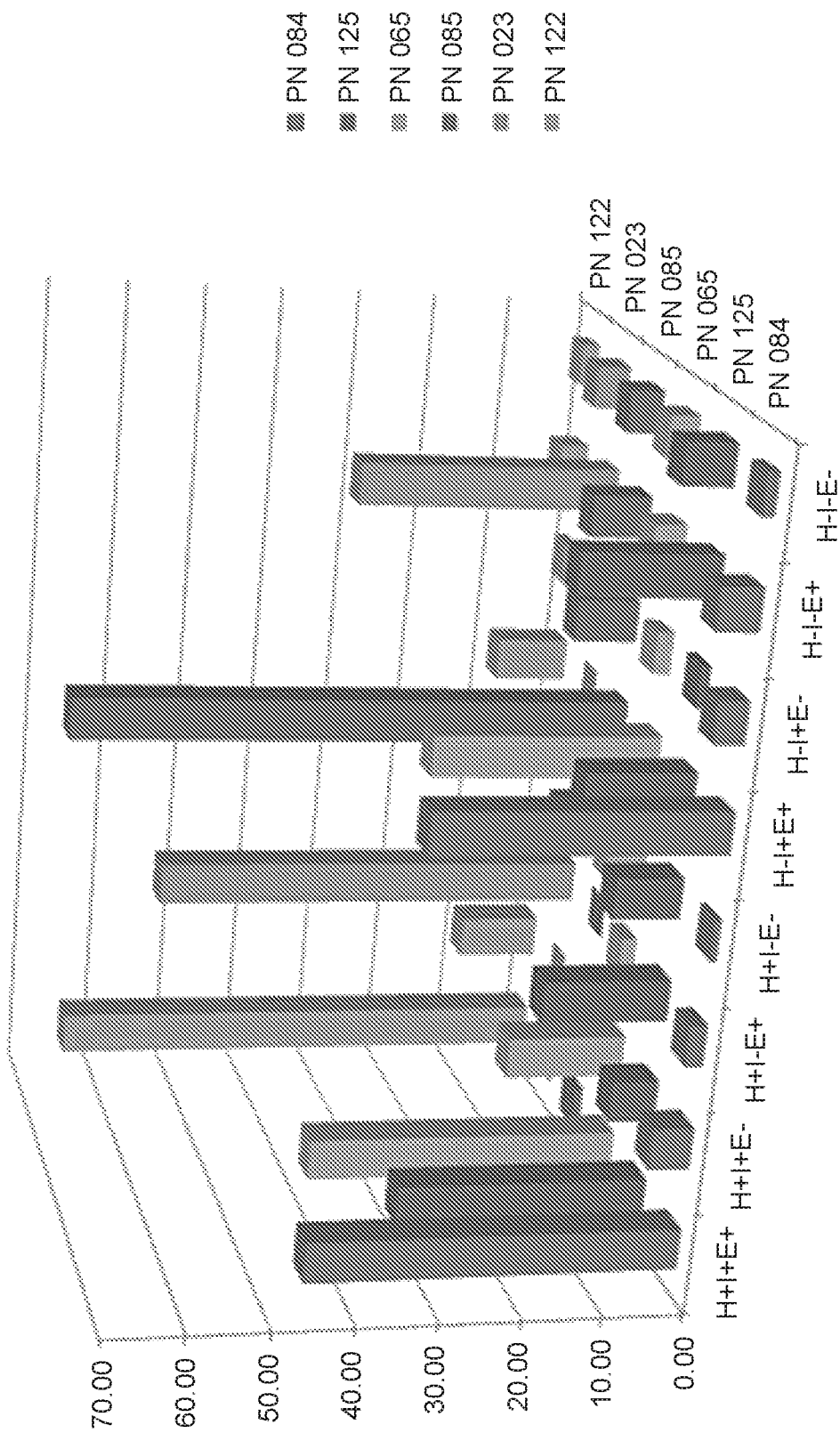
FIG. 2 demonstrates antigen expression profiles of six exemplary patients.

Analysis of an antigen expression profile from one patient is shown in FIG. 1. Antigen expression profiles of six patients cumulatively is shown in FIG. 2, where Her2 (H), IL13Rα2 (I), and/or EphA2 (E) are demonstrated. FIG. 3 demonstrates percentages of killed cancer cells with 1, 2, or 3 of the H, I, and E antigens when targeted with particular bispecific CAR T-cells. One can utilize mathematical models to describe both the heterogeneity of antigen expression in patients with GBM and to show that targeting all three TAAs produces a near-universal immunotherapeutic product for the treatment of GBM.

Example 3

Example of a Tricistronic Construct of Universal CAR Sequence

Figure 4:
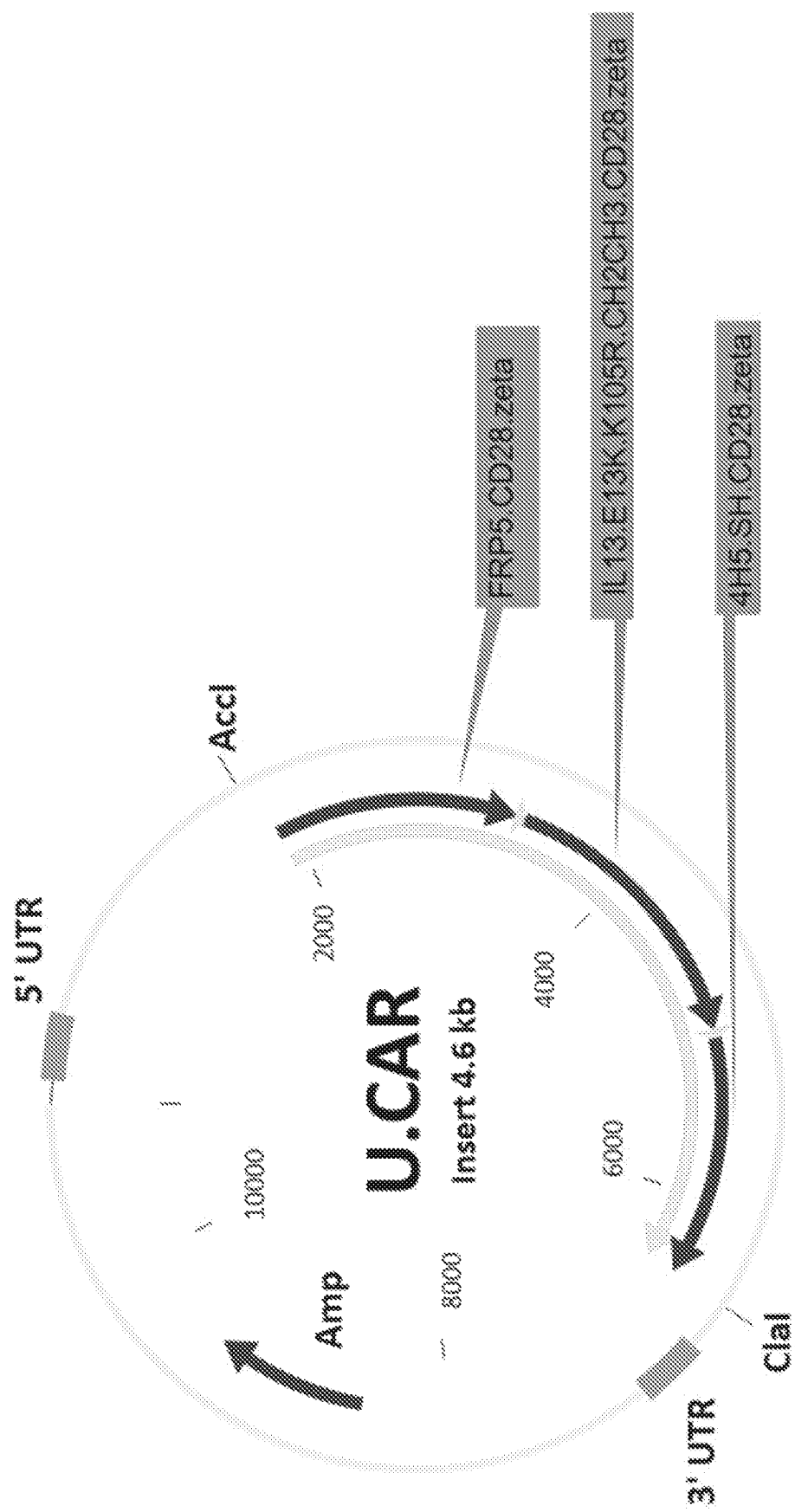
FIG. 4 illustrates an example of an expression vector that encodes three separate CARs on a tricistronic construct.

FIG. 4 shows an example of an expression vector that encodes three separate CARs on a tricistronic construct. In this particular embodiment, the size of the insert was 4.6 kb, which pushes the limits of capacity using a retroviral transduction system (as an example system). The vector utilizes gene sequences that had identical conserved regions, so codons were wobbled for optimization and to prevent recombination such that identical sequences <50 bps. The design included a proportionate and effective expression of three CAR molecules, with utilization of viral 2A sequences inserted between transgenes.

Leader sequences were inserted prior to all three CAR genes to effect migration of all three CARs on the cell surface of T cells.

Example 4

Simultaneous Detection of Three CAR Molecules

Figure 5:
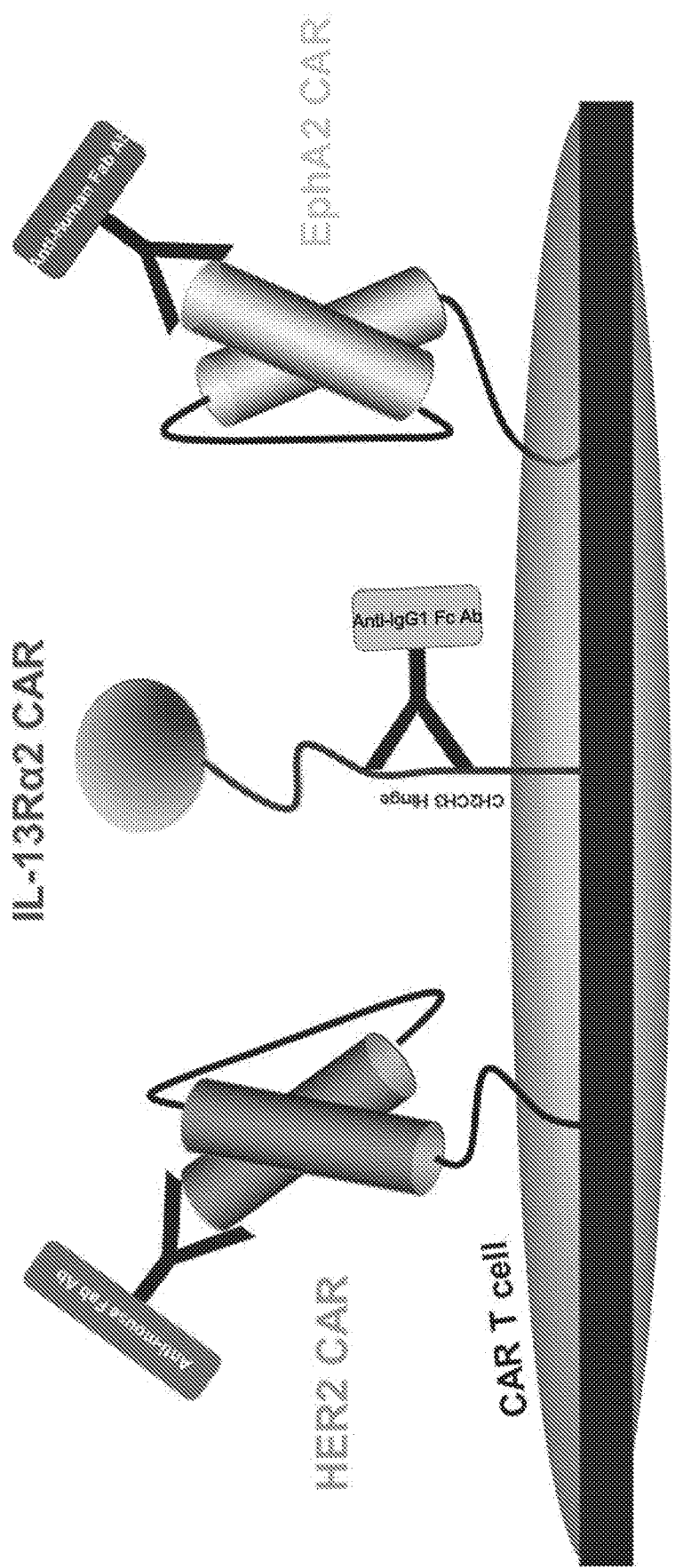
FIG. 5 illustrates simultaneous detection of three different CAR molecules on a single CAR T cell.
Figure 6:
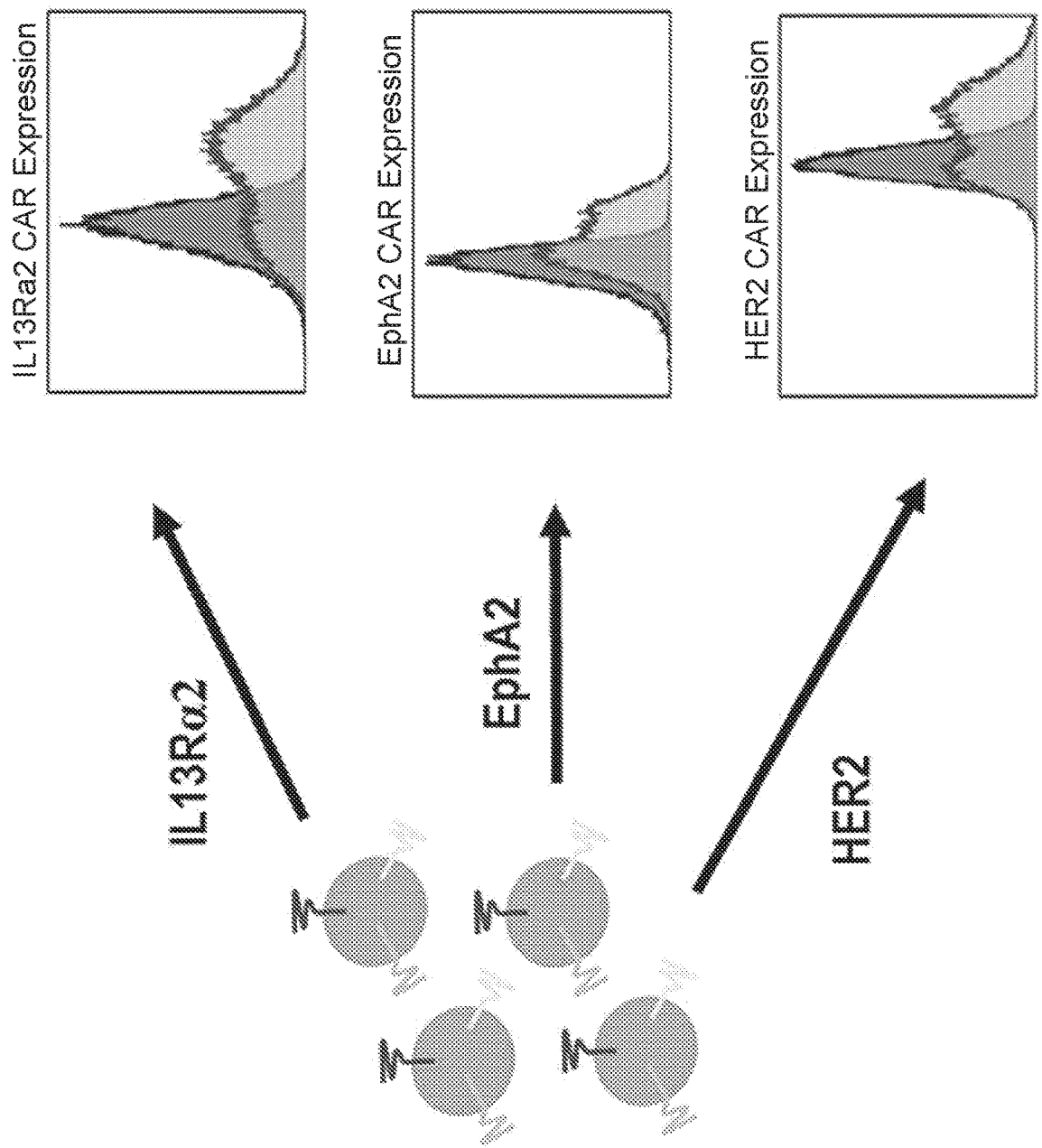
FIG. 6 shows FACS analysis for cells expressing the three separate CARs.
Figure 7:
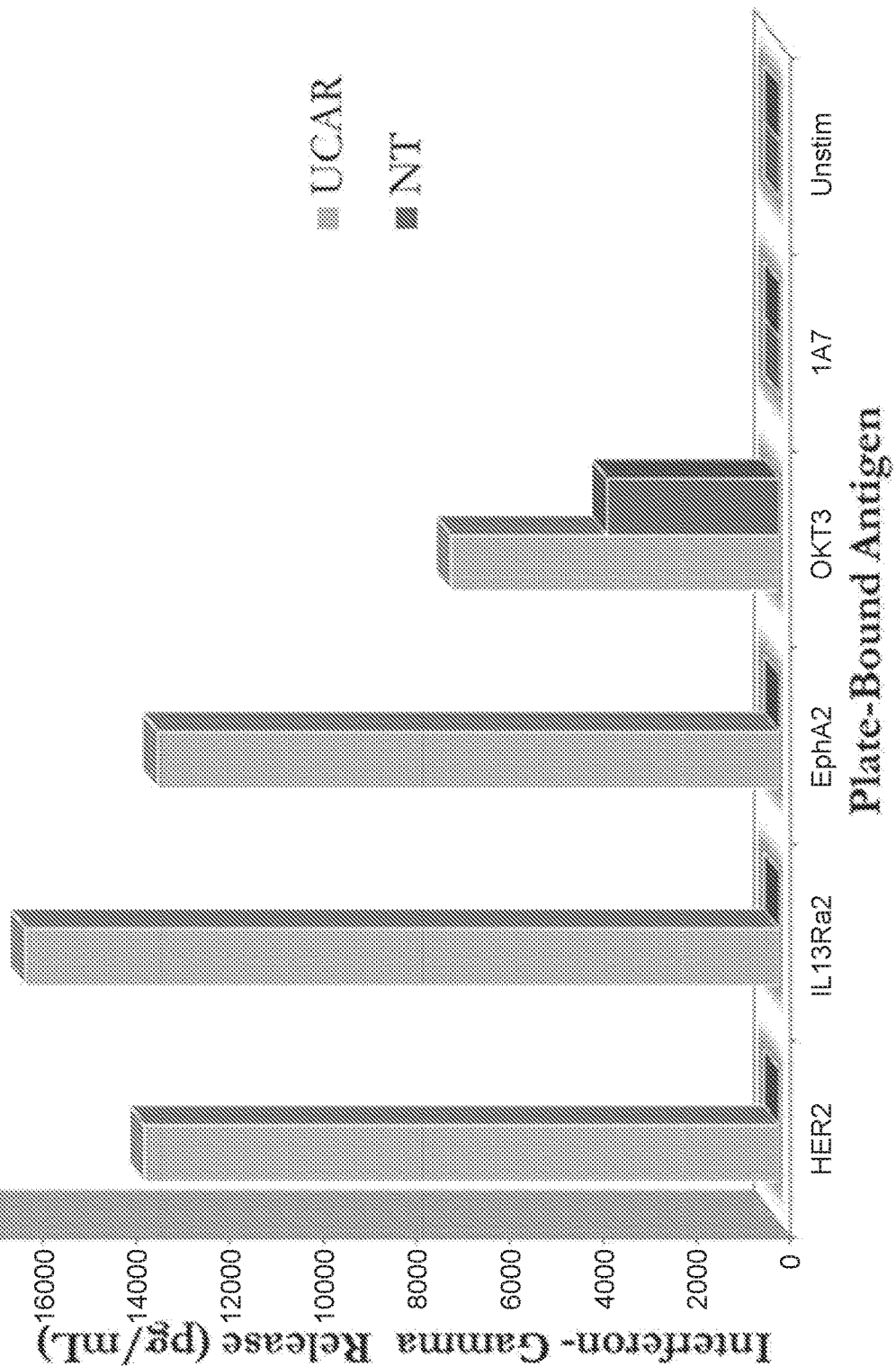
FIG. 7 shows that T cells separately expressing all three CARs are activated and proliferate specifically in response to three separate plate-bound glioma tumor antigens: HER2, IL13Rα2, and EphA2 utilizing IFNγ release as a measure.

FIG. 5 illustrates simultaneous detection of three different CAR molecules on a single CAR T cell utilizing, for example, an anti-mouse Fab antibody to detect HER2 CAR, an anti-IgG1 Fc antibody to detect IL13Rα2 CAR, and an anti-human Fab antibody to detect EphA2 CAR. FIG. 6 shows FACS analysis of expression of the three separate CARs. FIG. 7 shows that T cells separately expressing all three CARs are activated and proliferate specifically in response to three separate antigens (HER2, IL13Rα2, and EphA2, as examples), thus demonstrating that all of the CARs are expressed on the surface of the cells.

Example 5

Specificity of Activation and Proliferation of Universal CAR T Cells

Figure 8:
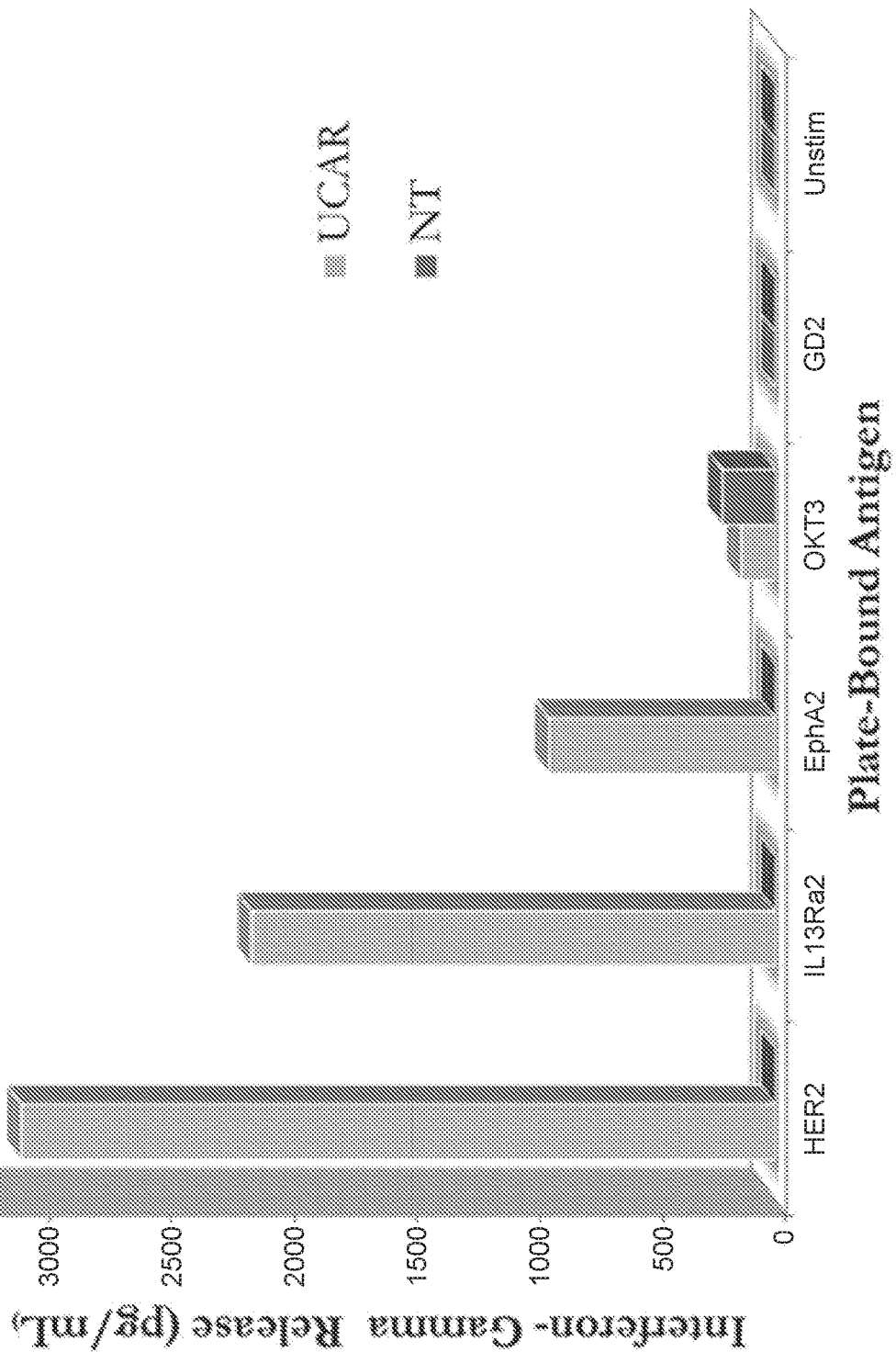
FIG. 8 shows that T cells separately expressing all three CARs are activated and proliferate specifically in response to three separate plate-bound glioma tumor antigens: HER2, IL13Rα2, and EphA2 utilizing IL2 release as a measure.

T cells separately expressing all three CARs are activated and proliferate specifically in response to three separate plate-bound glioma tumor antigens: HER2, IL13Rα2, and EphA2 (FIG. 7 and FIG. 8). FIG. 7 demonstrates IFNγ release and FIG. 8 demonstrates IL2 release.

Figure 9:
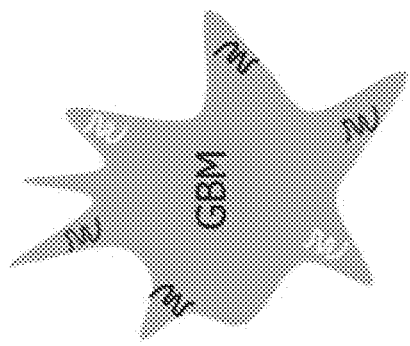
FIG. 9 illustrates comparison of a tri-specific product to a bi-specific product, pooled product, and uni-specific product for one or more patients (such as by activation, cytokine release and proliferation, cytolytic activity, ability to offset antigen escape).
Figure 9:
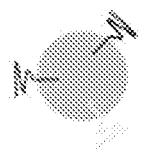
Figure 9:
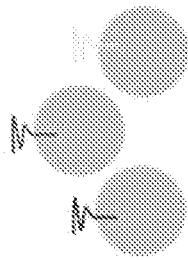
Figure 9:
Figure 9:

In particular embodiments, one can force-expression of Raji cells with single positivity for each of the three tumor antigens to test specificity of cytolytic function. One can also test in vitro function with autologous samples: one can compare tri-specific product for each patient to the optimal bi-specific product, pooled product, and uni-specific product for each patient (such as by activation, cytokine release and proliferation, cytolytic activity, ability to offset antigen escape) (FIG. 9).

One can also characterize the anti-tumor effect and survival advantage of a universal product compared to optimal unispecific products using in vivo autologous orthotopic murine models. One can treat recurrences from mice treated with single CAR T cells with universal product. This embodiment can be optimized for intracranial delivery to patients.

Example 6

Universal CAR T Cells Offset Antigen Escape and Treat Tumor Recurrence in Glioblastoma Introduction—Glioblastoma (GBM) is the most common and most aggressive primary brain malignancy and is virtually incurable. With the current standard-of-care, maximum feasible surgical resection followed by radical radiotherapy and adjuvant temozolomide, patients have a median survival of 14.6 months from diagnosis in molecularly unselected patients. Numerous target antigens that are overexpressed in GBM cells including HER2, IL13Rα2 and EphA2 have been identified. Targeting of HER2 using CAR grafted T-cells has been achieved, and their robust antitumor activity in animal models of human disease has been demonstrated. T cells modified to target HER2 kill primary high grade gliomas (HGG) and HGG stem cells, and induce regression of autologous orthotopic xenografts. To redirect the specificity of T cells, Chimeric Antigen Receptors (CARs) are utilized, which are artificial fusion molecules with an antigen-recognition extracellular domain usually derived from an antibody to an intracellular ζ-signaling chain of the T cell receptor. Further, a phase I/II clinical trial has recently been completed in which 17 adolescent and adult patients with progressive or relapsed GBM were infused systemically with autologous CTV-specific CTLs modified with a HER2-directed CAR showing a favorable safety profile and promising responses.

To further refine this approach it was investigated why tumors recurred in ~40% of experimental animals, and the emergence of an antigen-escape tumor cell population was discovered. These cells maintained positivity for two other validated glioma antigens, IL13Rα2 and EphA2. Recent data from primary gliomas described the GBM antigenic landscape in a small cohort of primary patient samples with a mathematical model indicating that there is a clear advantage for simultaneous targeting of a second antigen when specific antigen pairs that vary with each tumor are chosen. T cells co-expressing two distinct CAR molecules offset antigen escape and exhibited enhanced functionality. It was considered that there would be significant intra-patient and inter-patient variability in antigenic constitution with a larger cohort of primary GBM samples analyzed by flow cytometry to the extent that generating permutations of bispecific T cell products will preclude the successful translation of this approach into the clinic. It was further considered that a single T cell co-targeting all 3 antigens simultaneously could further increase the odds of complete tumor elimination in all tumors and offer enhanced anti-tumor activity.

The antigenic landscape in patient glioblastoma exhibits both intratumoral and inter-patient heterogeneity—Glioblastoma show substantial inter-patient variability in surface expression of numerous glioma-restricted antigens. However, the inter-patient hierarchy of expression and intratumoral antigen expression pattern within a cohort of patients has not been well characterized. Studies herein concern the simultaneous expression pattern of three established glioma-restricted antigens (HER2, IL-13Rα2, and EphA2) in primary GBM samples. Multicolor flow cytometry was utilized to study the antigen expression in cultured tumor cell populations and to further describe such patterns in sub-populations obtained from tumor sections.

Figure 10A:
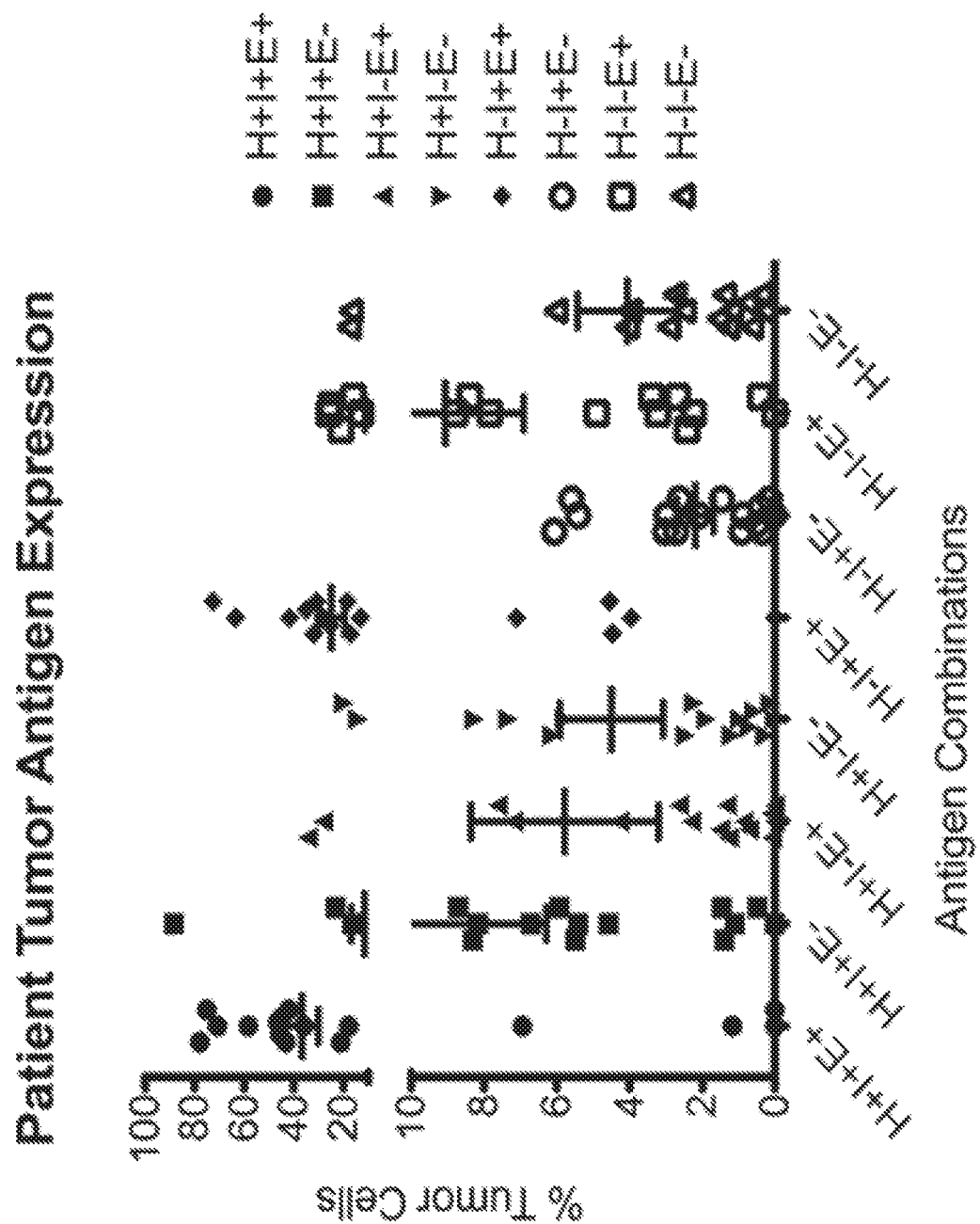
FIG. 10A shows distribution of antigenic expression between 16 primary glioblastoma cell lines by percentage of cells expressing each possible combination.
Figure 10B:
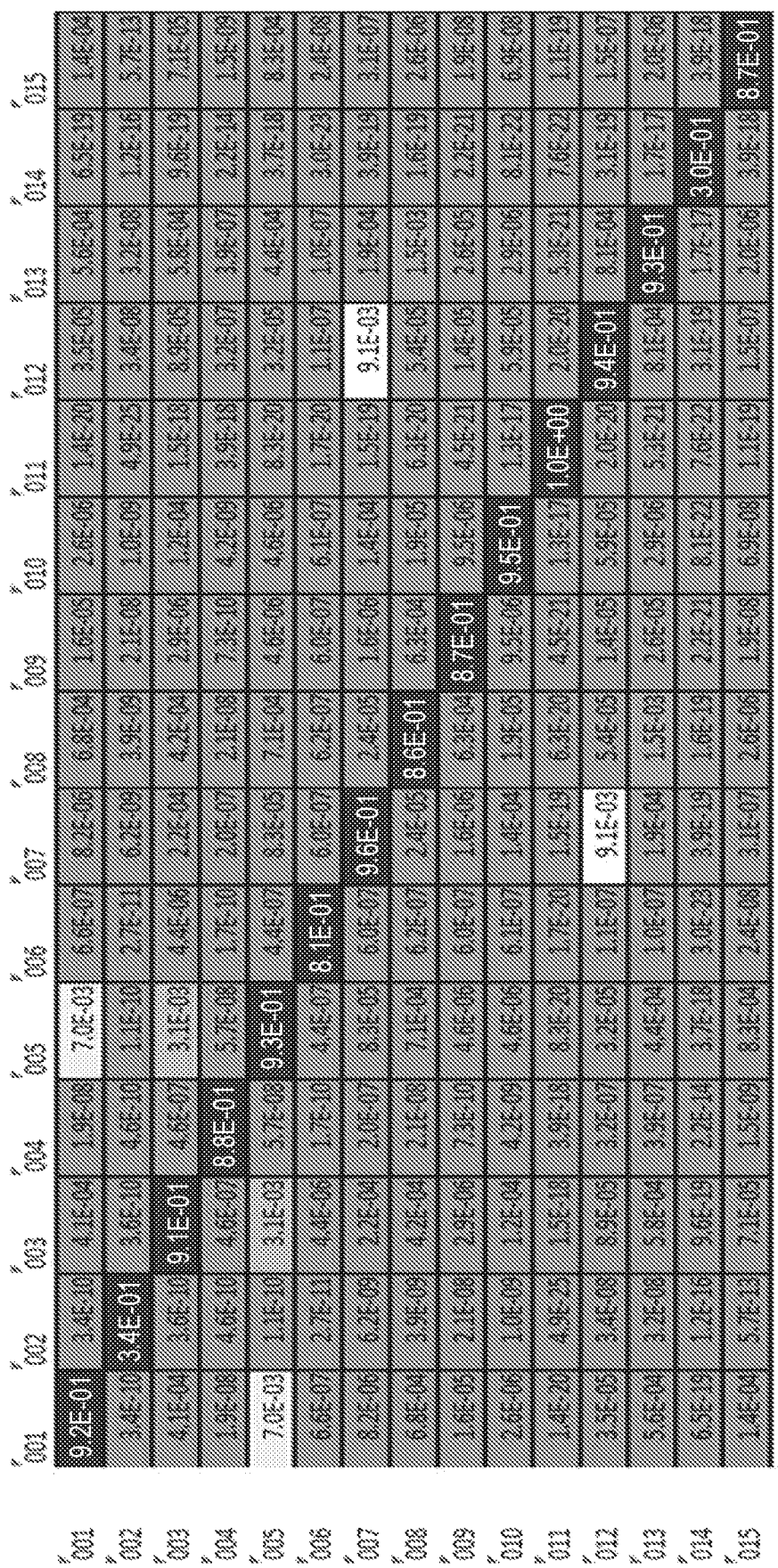
FIG. 10B shows comparison of the distribution between each patient with a log rank test.
Figure 10C:
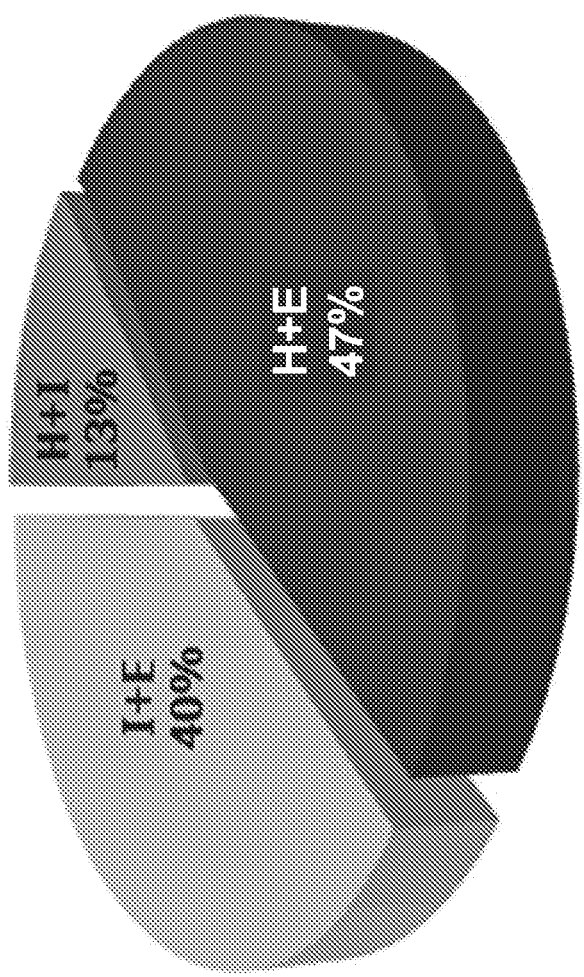
FIG. 10C provides percentage of patients for which each if the different bispecific combinations would target the largest number of cells.

To characterize single cell expression patterns in homogenized tumor cell populations, approximately 100,000 primary GBM cells were simultaneously interrogated for HER2, IL-13Rα2 and EphA2 using flow cytometry (FIG. 10A). Combinations of cells within a single tumor expressing each possible combination of the three above antigens differed significantly ($p=4.9 \times 10^{-25}$ to $9.1 \times 10^{-3}$) for all samples examined (FIG. 10B). Additionally, all three possible combinations of the optimal combination of two antigens that could be targeted to give the highest probability of tumor elimination were found in the patient cohort (FIG. 10C).

These findings led to the consideration that the degree of variability in the optimal bispecific combinations between patients and the limitations in having to produce different permutations of bispecific combinations between patients justifies targeting all three glioma antigens with one immunotherapeutic product. In specific embodiments, this product leads to better tumor cell killing and offsets antigen escape by extending the reach of effectors to the overwhelming majority of tumor cells in all patients. The data showed that the odds of capturing the bulk of tumor cells by targeting three antigens simultaneously are far superior in its broad therapeutic reach to all patients.

Successful Simultaneous Expression of CAR Molecules Specific for HER2, IL13Rα2 and EphA2 Encoded by a Single Transgene in GBM Patients' T Cells It was considered that a strategy targeting all three glioma antigens would be advantageous. It was aimed to express three different CAR molecules each targeting either HER2, IL13Rα2 or EphA2 simultaneously and proportionately on the surface of T cells in a single transgene to create a "universal" therapy (UCAR T cells) that targets an overwhelming majority of the cells for all patients with GBM, although this therapy could be utilized to target three or more antigens in individuals with other types of cancer.

Figure 11A:
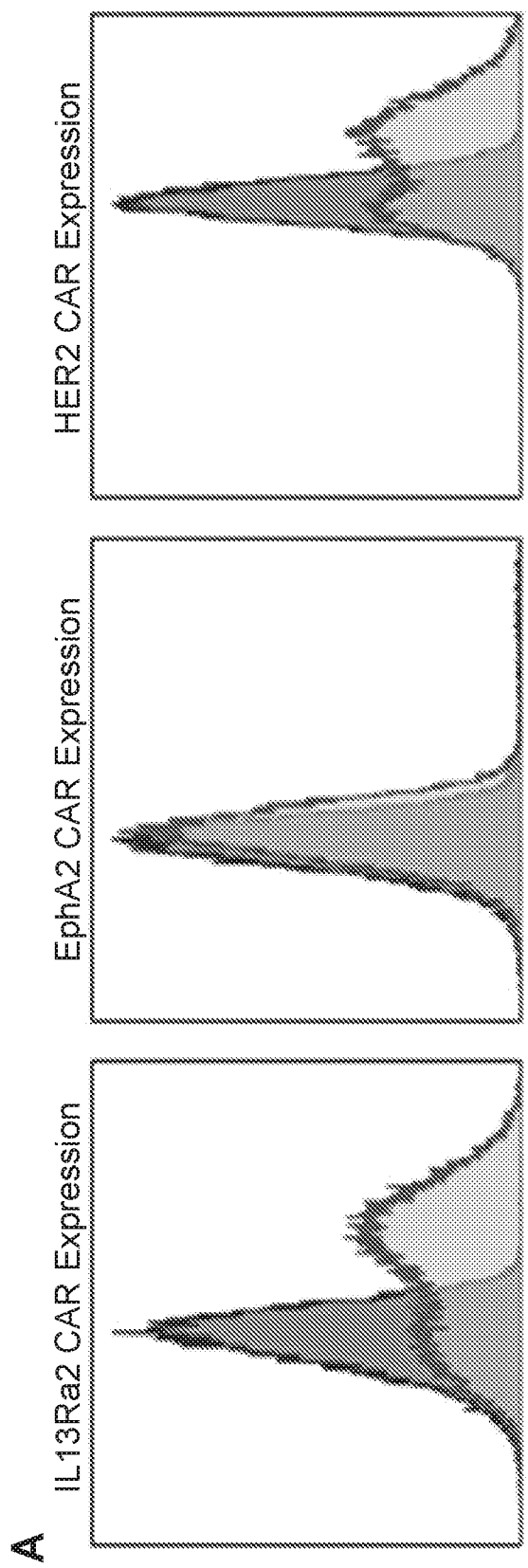
FIG. 11A shows surface expression of three different CAR molecules by flow cytometry in one donor and FIG. 11B provides analysis of donor T cells for simultaneous expression of multiple CAR molecules by flow cytometry.
Figure 11B:
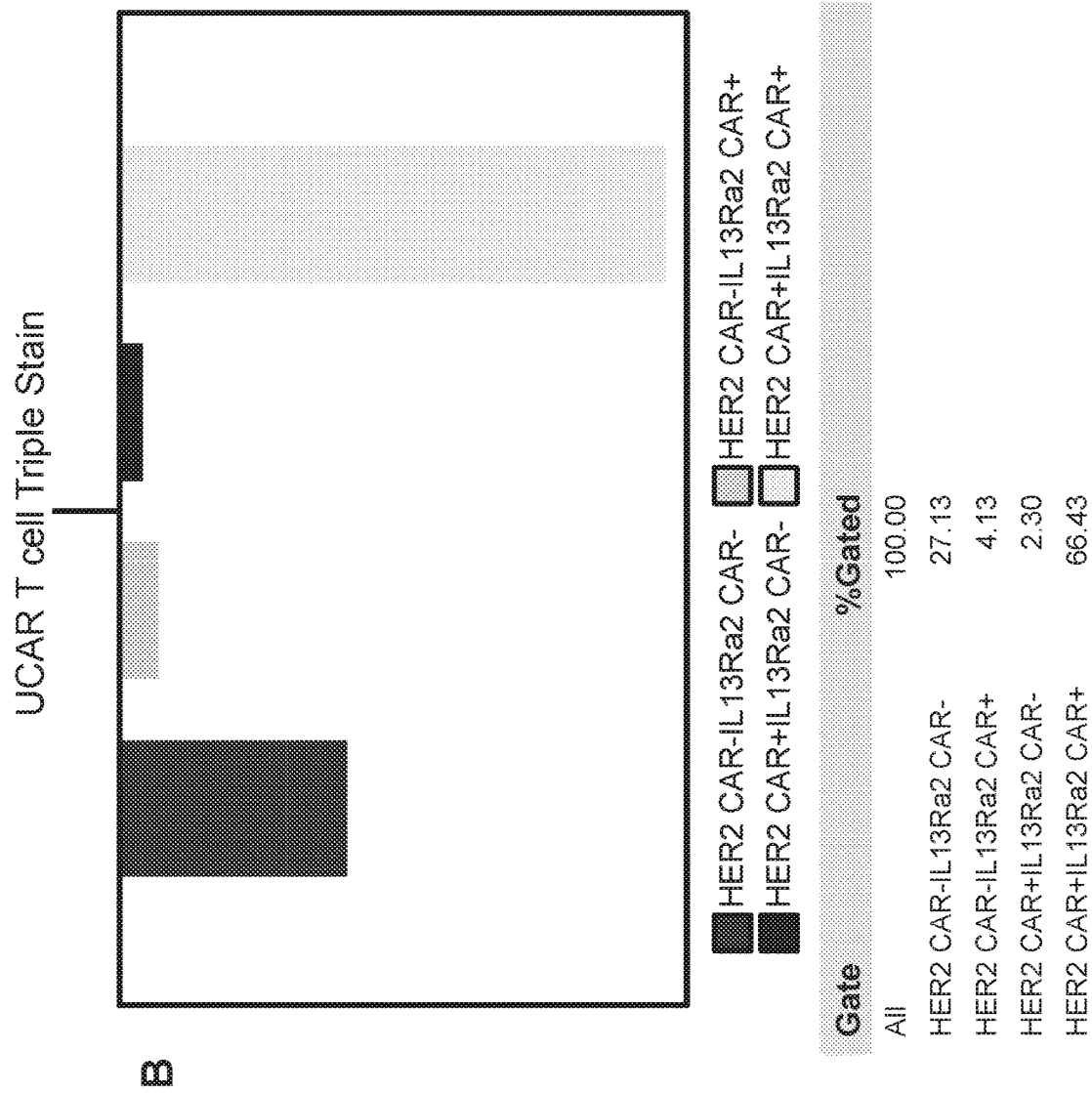

There has been exploration of strategies to co-deliver multiple transgenes using retroviral constructs expressing 2A sequences. A DNA construct was generated that successfully packages 3 second generation CAR-encoding transgenes using a retroviral system to achieve proportionate and reliable delivery. Two of the CAR molecules were detected simultaneously by flow cytometry analysis on the surface of approximately 60% of T cells transduced in two separate donors (FIG. 11A). Additionally, 66% of the cells that expressed any CAR molecule expressed both the HER2 CAR and IL13Rα2 CAR (FIG. 11B).

UCAR T Cells Exhibit Distinct Functionality Against Each of Three Glioma Antigens.

The product shows expression of three CAR molecules each targeting different glioma surface antigens simultaneously on individual T cells. To test whether these T cells could recognize each of these three antigens distinctly, T cells were mixed with plate-bound antigen. To assess their proliferative capacity, non-transduced and UCAR T cells were made from each of two donor's PBMCs and were incubated in non-tissue culture plates coated with recombinant human HER2-Fc, IL-13Rα2-Fc, and EphA2 Fc. OKT3 stimulation was used as positive control and GD2-Fc and NT T-cells from the same donors exposed to the same antigens were used as negative controls. After incubating 24 hours, conditioned-culture medium were collected and analyzed for cytokine release by ELISA. These T cells activate and proliferate to plate-bound antigen stimulation as evidenced by detection of interferon-gamma (IFN-γ) and interleukin-2 (IL-2) release, respectively compared to these appropriate controls (FIGS. 7 & 8).

UCAR T Cells Recognize and Kill Antigen Positive Tumor Cells

Figure 12:
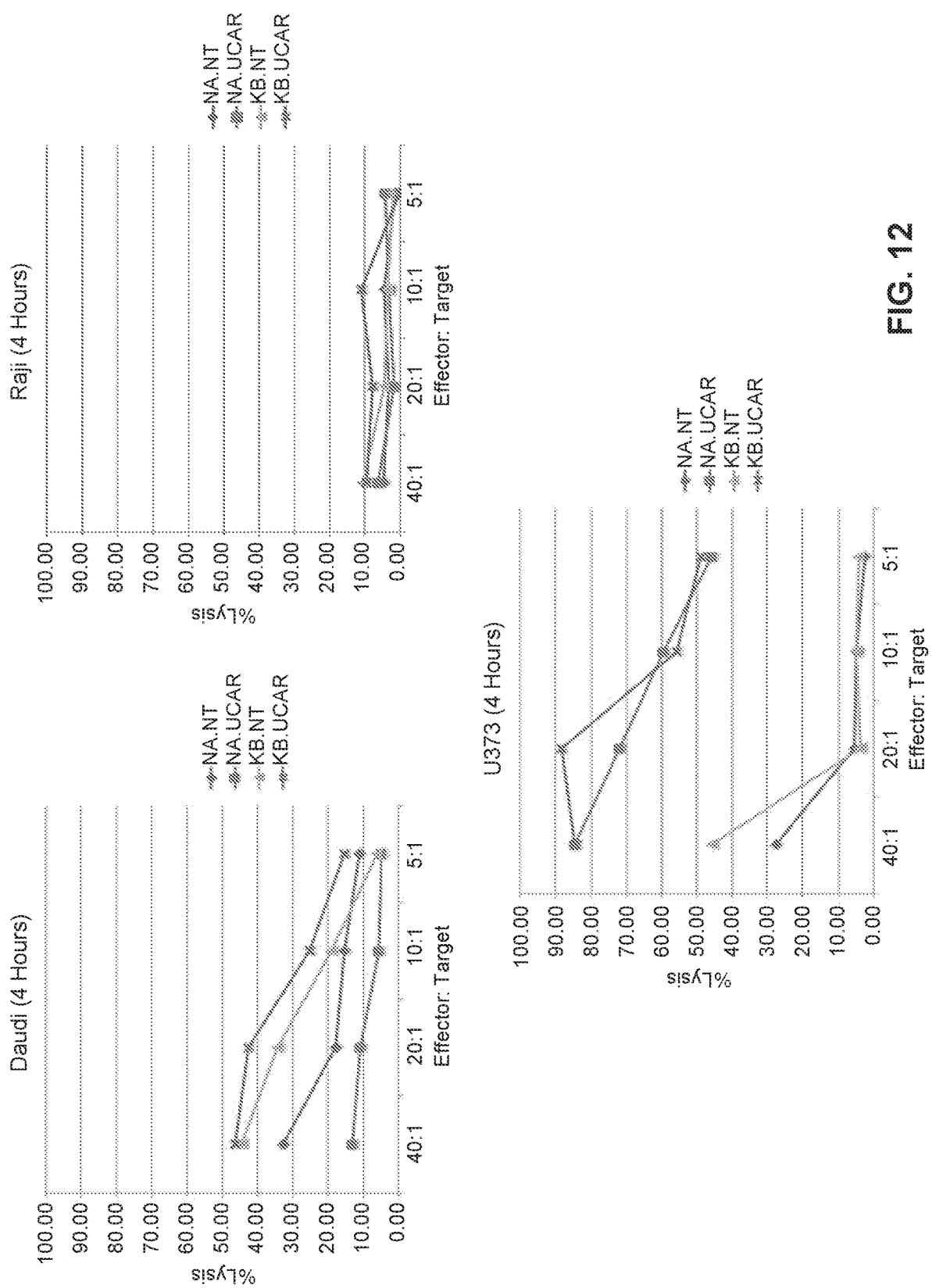
FIG. 12 shows 4-hour chromium$^{51}$ cytotoxicity assay showing tumor killing of U373 by UCAR T cells and minimal killing of Raji cells.

In addition to activation upon exposure to antigen, it was desired to show tumor killing upon recognition of each of the three tumor antigens. Numerous cancer cell lines were screened by flow cytometry to find lines that are positive for only one of the three antigens targeted—HER2, IL13Rα2, or EphA2. While no lines were singly positive for one antigen, two lines that were negative for all three antigens—Raji and Daudi cells—were tested to see if UCAR T cells could induce tumor killing. Raji cells were not significantly killed by the tri-specific product by 4-hour chromium[51] cytotoxicity assay and were thus selected as a platform to construct tumor cells positive for single tumor antigens (FIG. 12).

Figure 13:
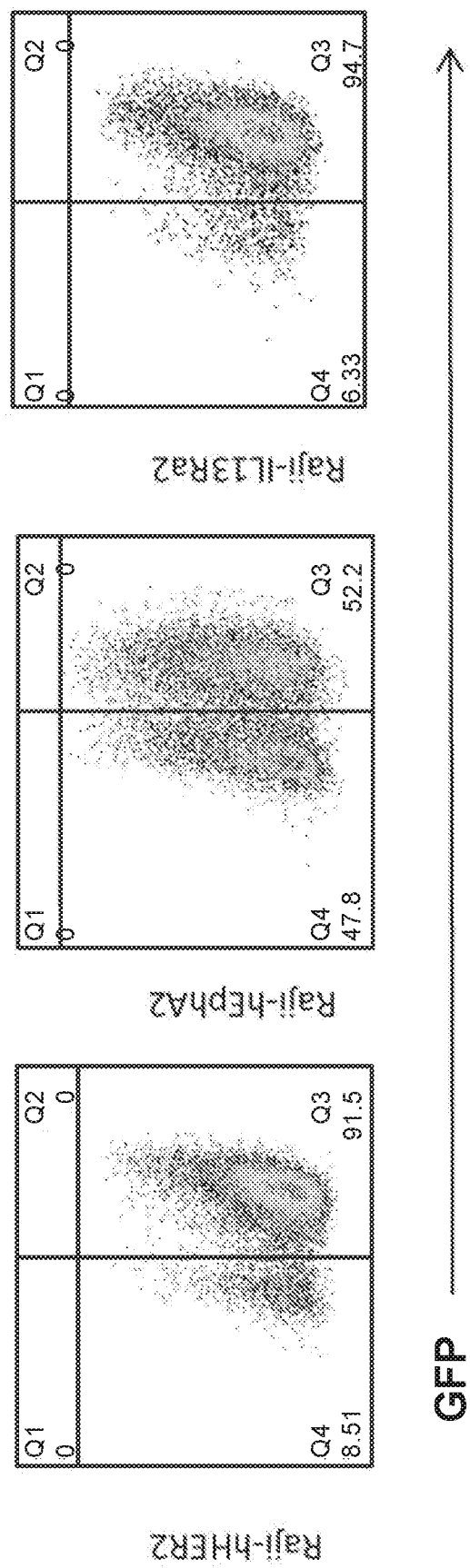
FIG. 13 shows expression of transgenes for tumor antigen measured by GFP expression.

Three separate Raji cell populations were genetically modified with a lentiviral vector encoding one of three tumor antigens and GFP—IL13Rα2 (Raji-IL13Rα2), HER2 (Raji-HER2, or EphA2 (Raji-EphA2). Non-transduced Raji cells were used as controls. Transduction efficiencies of 3-11% were obtained, and in order to create a more robust population of tumor cells the Raji were FACS sorted and grown in culture until an adequate number of cells with greater than 50% of the tumor antigen for each antigen was obtained by GFP measurement (FIG. 13). Single CAR T cells were constructed as controls to target only one of the specified tumor targets.

Figure 14:
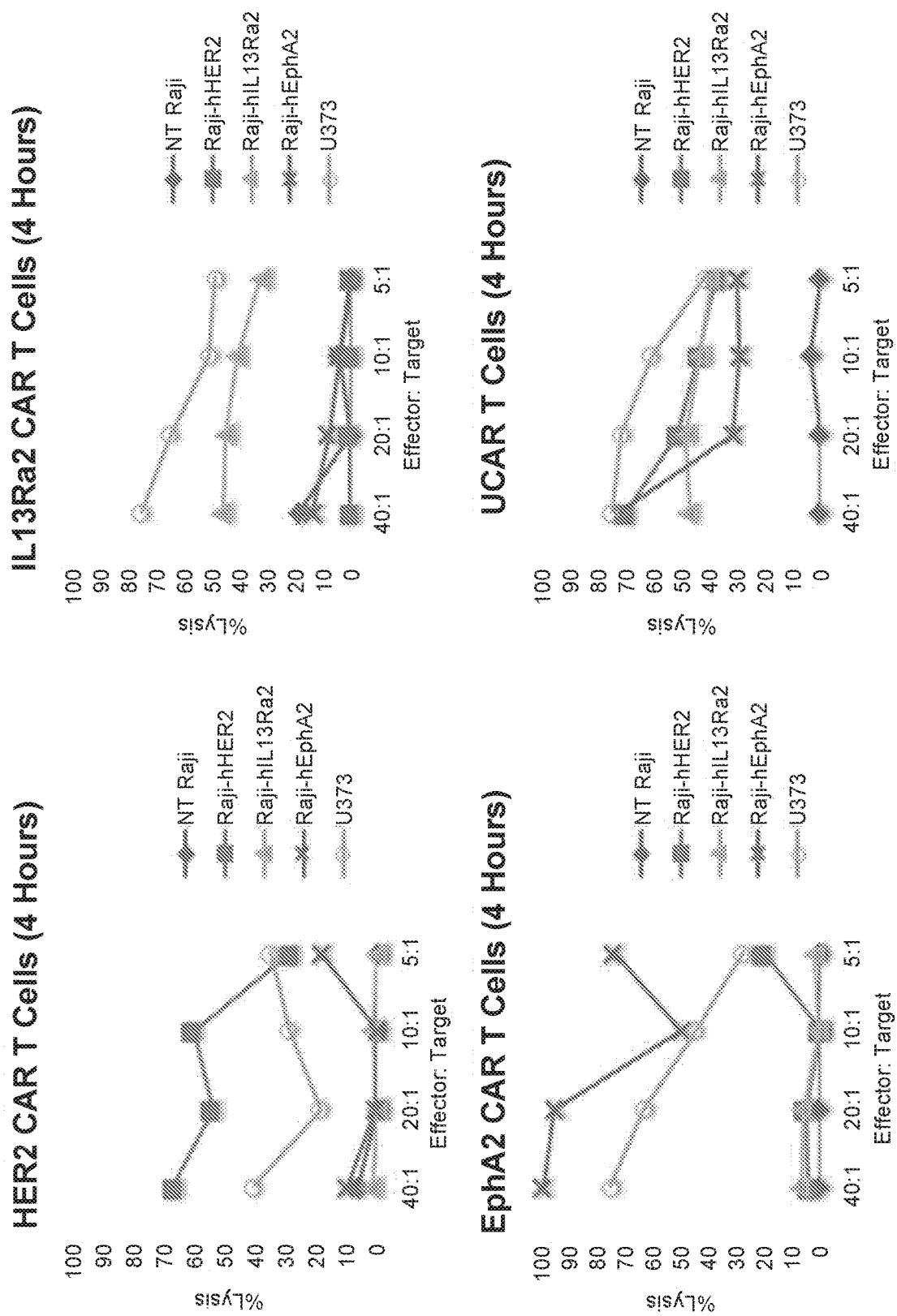
FIG. 14 shows 4-hour chromium 51 cytotoxicity assay showing UCAR T cells kill tumor cells positive for each of three tumor antigens—HER2, IL13Rα2, and EphA2.

UCAR T cells showed significant killing of cells positive for each of the tumor antigens individually, while T cells expressing only a single CAR molecule recognized and killed only the tumor cells expressing that particular antigen. It was thus concluded that the UCAR had distinct ability to activate and kill tumor cells positive for any of the three tumor antigens—HER2, IL13Rα2 and EphA2. Additionally, while the EphA2 CAR in this product is not detectable by flow cytometry, it was concluded that because of its equivalent activation and proliferation in these in vitro models that this CAR is present on the surface, likely proportionate to the other two detected CAR molecules (FIG. 14).

Figure 15:
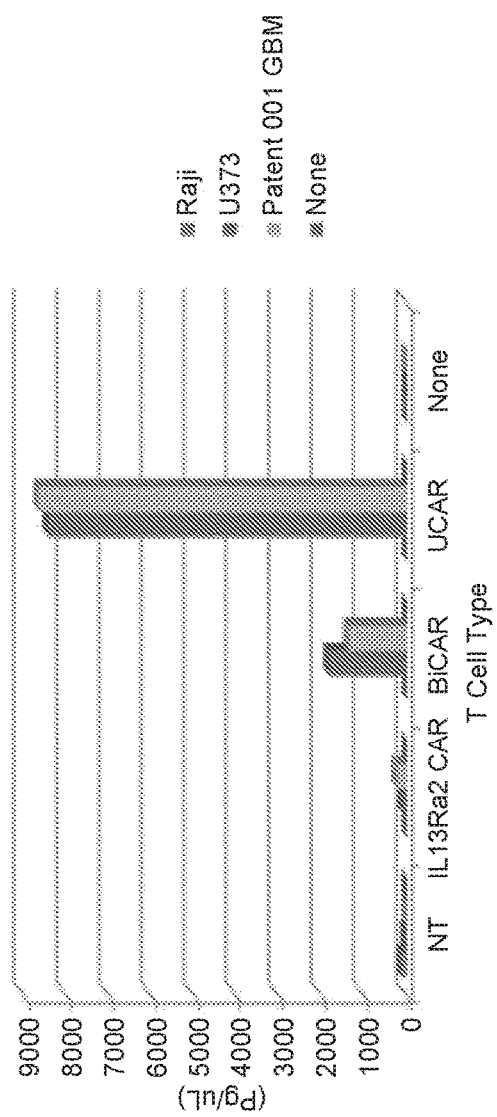
FIG. 15 shows IFN-gamma and IL2 release by patient T cells transduced with various types of CAR molecules exposed to patient glioma cells in co-culture.
Figure 15:
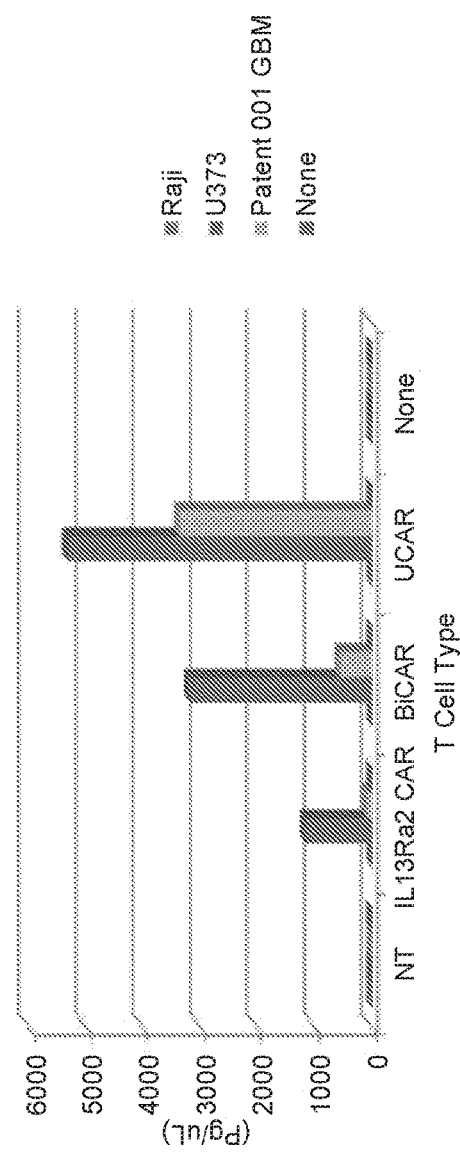

Universal CAR T Cells Exhibit Enhanced In Vitro Functionality Compared to Uni- and Bi-Specific Products It was considered that the trispecificity conferred by targeting three tumor antigens would lead to improved activation and anti-tumor efficacy of UCAR T-cells an in-vitro autologous experiment. For one patient, the optimum unispecific and bispecific antigen combinations from their tumor antigen analysis were used to construct T cell variations. To assess their proliferative capacity, non-transduced, optimum unispecific and biCAR T-cells, and UCAR T cells made from each patient's PBMCs and were co-cultured with both the patients cultures GBM cell line and U373 cells in 1:4 (tumor cell:T-cell) ratios. After incubating 24 hours, conditioned-culture medium were collected and analyzed for cytokine release by ELISA. Both IFN-γ and IL-2 secretion were significantly higher with biCAR T-cells in comparison to unispecific T-cells and their pooled-product (FIG. 15).

Figure 16:
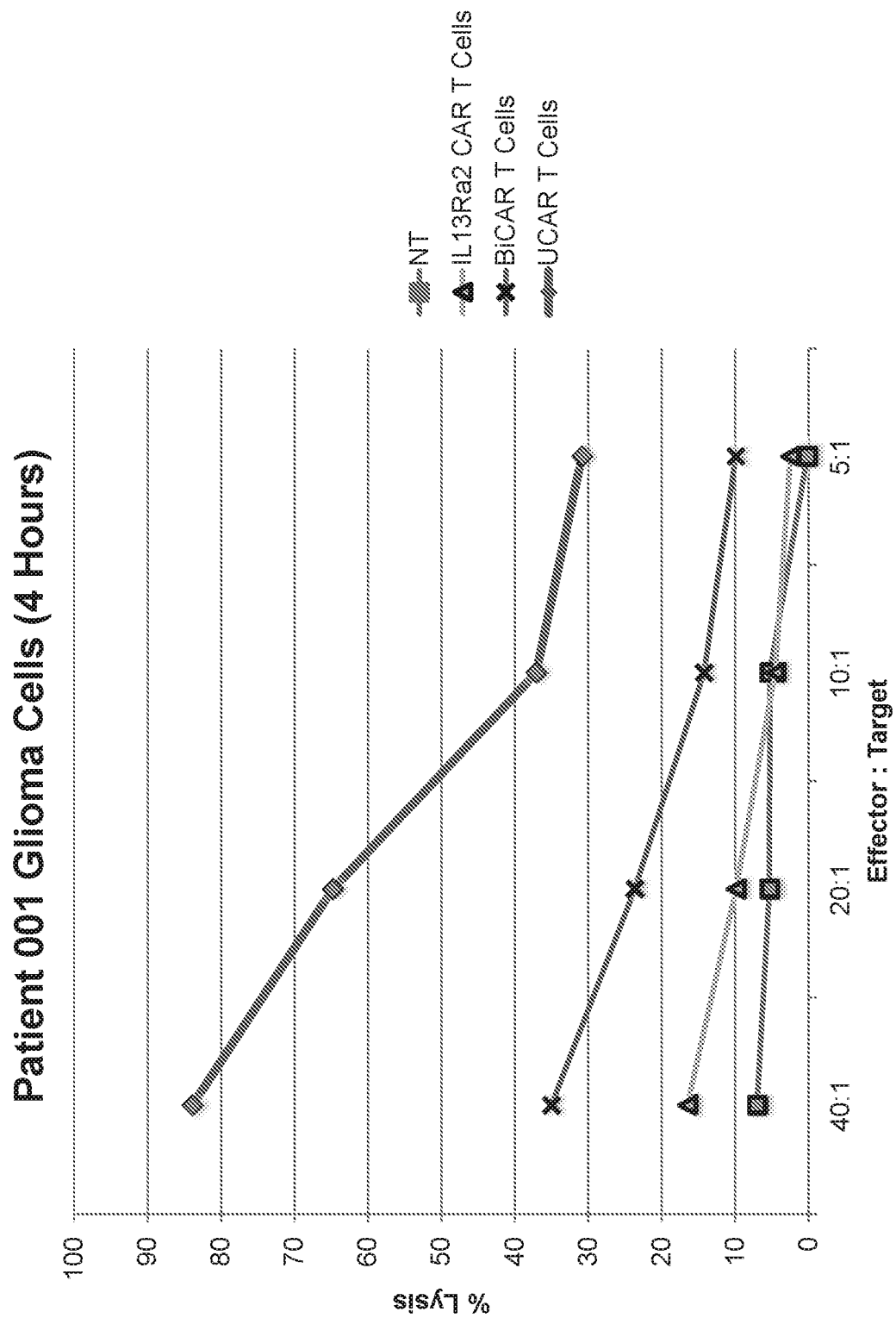
FIG. 16 shows patient T cells expressing 3 different CAR molecules have enhanced cytotoxicity compared with those expressing one or two different CAR molecules by chromium$^{51}$ assay.

To assess their cytolytic activity, patient cultured a chromium$^{51}$ cytotoxicity assay was performed as GBM and U373 cells were co-cultured with non-transduced, optimum unispecific and biCAR T-cells, and UCAR T cells. After incubating 4 hours, cultures were analyzed for chromium release. UCAR T cells showed significantly higher cytolytic activity than other T cell permutations at all T cell to tumor ratios. Further, the addition of additional CAR T cells enhanced tumor killing as bispecific T cells showed significantly higher tumor killing compared to unispecific variations (FIG. 16).

Collectively, these ex-vivo results indicate that a trispecific product targeting HER2, IL13Rα2 and EphA2 result in enhanced functionality.

Visualization of the UCAR/GBM Interface Reveals Enhanced Antigen Clustering and Cytoxicity.

CAR T cells are required to engage in an active interaction with specific target antigens on tumor cells to form an immunological synapse (IS), which then results in lytic killing. To further investigate if the UCAR T cells were trispecific in nature, the localization of the tumor antigens at the CAR T cell-GBM contact point was determined. UCAR, HER2 CAR and non-transduced T cells were incubated with U373-GBM cells, and then stained for HER2, IL13Rα2, and EphA2. When visualized using three dimensional confocal microscopy and z-stacking of 0.2 micron slices taken through the T cell to tumor cell conjugate to cover the entire volume of the IS, all three antigen were found to cluster at the IS/contact point between the effector and tumor cell for the TanCAR-GBM conjugates. IS selected as a specific sub-region of interest shown as 1×1 μm voxel spanning the interface of contact between the two cells, while only HER2 localized to the IS for the HER2 CAR T cell-GBM conjugates, respectively, thus implying the UCAR cells to be trispecific in nature. Using a fixed intensity threshold for all conjugates analyzed, quantification of receptor accumulation at the IS revealed that there was an increased clustering of all three antigen at the synapse of the UCAR cells compared to that of HER2 CAR alone. Non-transduced T cells showed significantly lower levels of receptor clustering for all three antigen at the synapse. The NT-GBM interface could demonstrate the amount of receptors normally present at the surface of a non-targeted tumor cell at any given time. It has been established that tumor antigen density can correlate with functionality, the grouping of three antigen at the IS could reflect a mechanism of enhanced antitumor function.

Figure 17A:
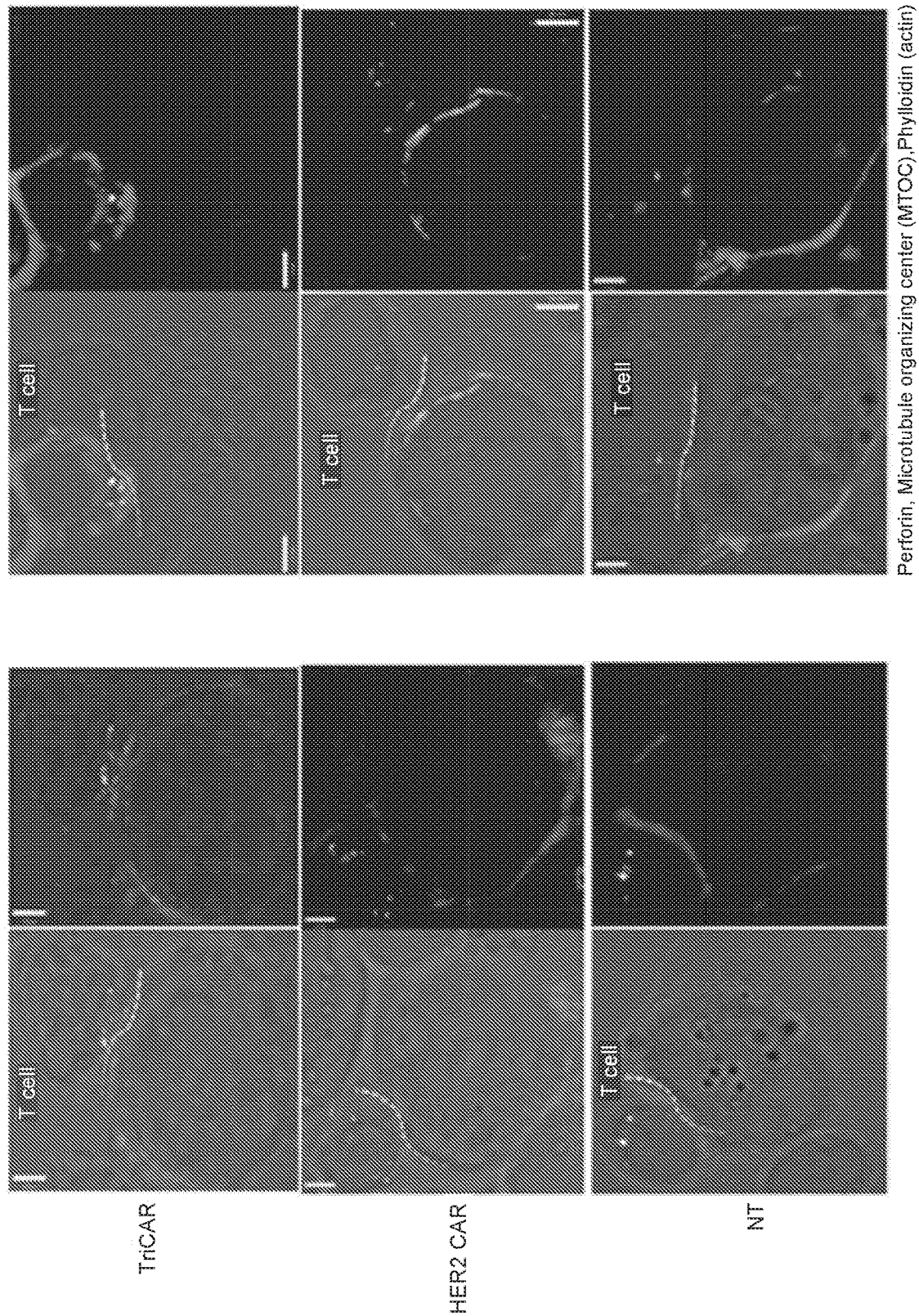
FIG. 17A shows conjugates of U373 and TriCAR/Her2CAR/Nontransduced T cells with U373 cells. Dotted line indicates Immune synapse (IS)
Figure 17B:
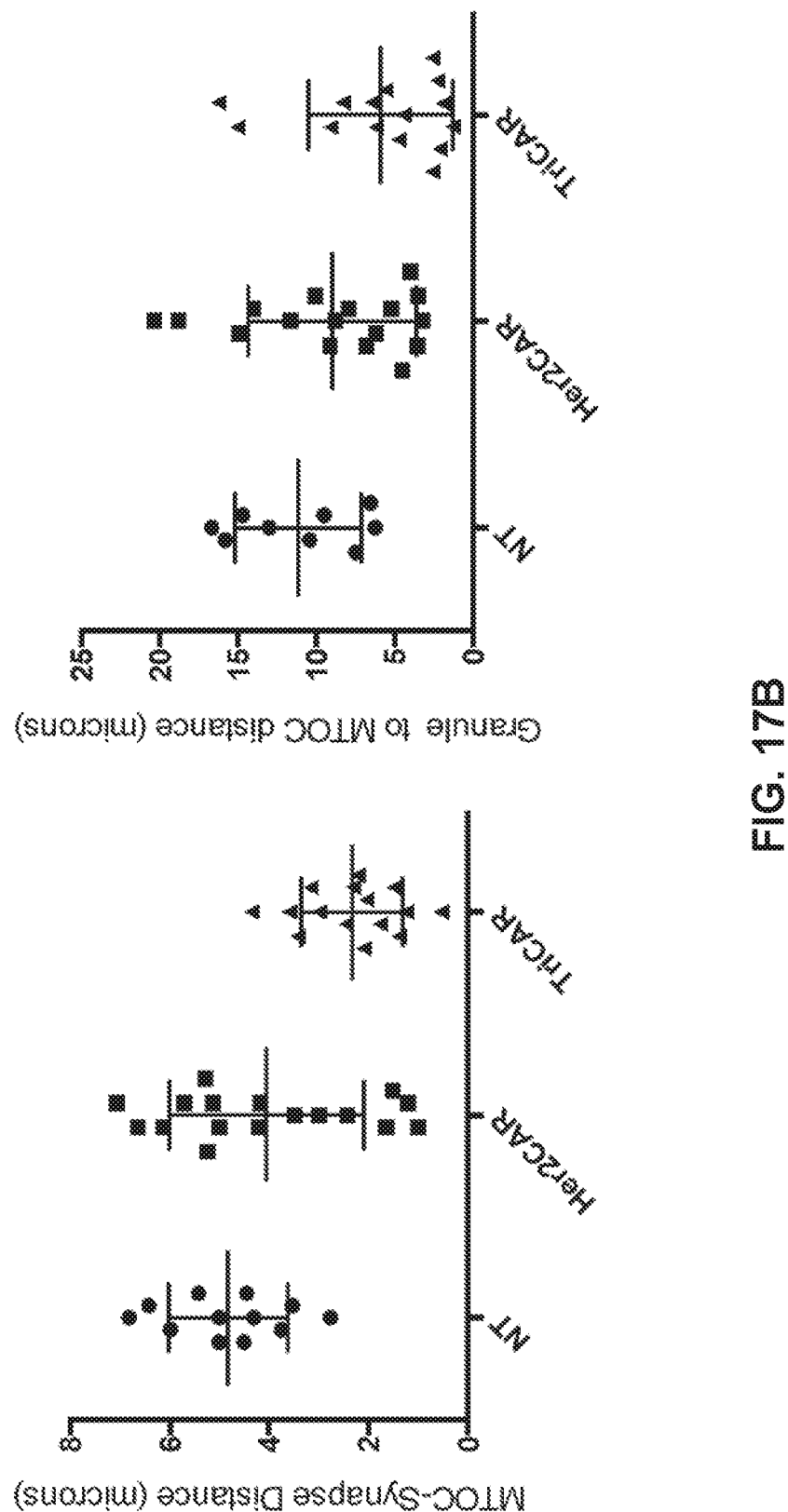
FIG. 17B shows distance of MTOC from IS measured (indicating cytolytic potential of T cell).

Further, perforin quantification, f-actin quantification, and microtubule organizing center (MTOC) mobilization at the IS all indicate enhanced cytotoxic function. U373 cells were stained for perforin, phylloidin, and the microtubule organizing center (FIG. 17A). They were then co-cultured with non-transduced, HER2 CAR, and UCAR T cells. Compared to NT T cells and HER2 CAR T cells, UCAR T cells had significantly less distance on average between the synapse and the MTOC, indicating more advanced mobilization to the IS (FIG. 17B). The convergence of granules is not significantly different from the Her2CAR but still much higher than NT cells. As granule convergence is an early step in lytic killing and happens before movement of the MTOC to the synapse, the difference in MOTC distance might reflect a late and not early phenotype. These findings represent the enhanced IS organization and correlates with cytolytic function.

Significance of Certain Embodiments—

Having observed the antigenic landscape of these tumors, it was considered to use a multispecific yet still targeted approach to parallel this intricate hierarchy of antigenic expression by targeting all three validated antigens studied. This approach generated a cellular product for adoptive immunotherapy that would has a spectrum of therapeutic reach broad enough to encompass the inter-tumoral variability observed and thus represents a "universal" therapeutic T cell product in GBM.

While this product itself could swiftly move to clinical trials, the optimization of a multispecific T cell product for GBM may include other IL13Rα2 CAR to minimize the risk of off-target effects, modifying or adding signaling domains to promote persistence of T cells or prevent exhaustion, adding a safety mechanism in the event of severe adverse events, or including or exchanging for other known GBM tumor antigens, such as EGFRvIII.

Additionally, this evidence is applicable to other diseases. While CAR therapy has shown lasting remissions in patients with relapsed acute lymphoblastic leukemia, failure of CD19 CAR T cell therapy has been associated with development of a CD19-tumor clones that may represent escape variants. The probability of antigen escape may be reduced if T cells are engineered to recognize multiple disease-specific B-cell antigens—such as CD22, CD20 or ROR1—in addition to CD19. In a wide spectrum of cancers multiplex targeting with T cells targeting a combination of tumor antigens represents a platform to impact outcomes by targeting tumor tissue specifically while preventing escape variants.

Methods

Blood Donors, Primary Tumor Cells and Cell Lines.

Blood samples and primary tumor cells were obtained from healthy donors and patients with GBM respectively, on a protocol approved by the IRB of Baylor College of Medicine and The Methodist Hospital. The U373-GBM cell line was purchased from the American Type Culture Collection (ATCC) and grown in DMEM with 10% FCS, 2 mM GlutaMAX-I, 1.5 g/L sodium bicarbonate, 0.1 mMol/L nonessential aminoacids, and 1.0 mMol/L sodium pyruvate. T-cells were maintained in T-cell media (250 mL RPMI-1640, 200 mL CLICKS with 10% FCS containing 2 mMol/L GlutaMAX-I).

Tumor samples were processed aseptically and primary cell cultures were initiated using DMEM with 15% heat-inactivated FCS, 2 mM GlutaMAX-I, 1% Insulin-Transferrin-Selenium-X supplement, and 1% Penicillin-Streptomycin mixture (all media and supplements from Invitrogen). Cells were used within 7 days of plating or established as primary cell lines.

Construction, Delivery and Expression of the UCAR-Encoding Transgene.

The IL13Rα2 binding IL13-mutein, HER2-specific scFv, FRP5, and EphA2-specific scFv, 4H5, have previously been described. The modeled bispecific extracellular-domain was assembled on Clone Manager® (Sci-Ed Software, Cary, N.C.). The designed transgene DNA sequence was modified to include restriction enzyme sites at the cloning sites and exclude any inadvertently inserted sites within the translation elements, then optimized using the GeneOptimizer® software for maximum protein production. The UCAR extracellular-domain was then synthesized by GeneArt® Inc. using oligonucleotides, cloned into the Gateway® entry vector pDONR™221, and sequence-verified. This antigen recognition domain was then sub-cloned in frame into an SFG retroviral vector containing a short hinge, and the transmembrane and signaling domain of the costimulatory molecule, CD28 and the ζ signaling domain of the T cell receptor. The structure of the construct was confirmed using restriction digests. The 5'-3' as well as the 3'-5' sequence of the whole construct was confirmed using single base pair pyro-sequencing (SeqWright DNA-Technology, Houston, Tex.) with >97% homology with the optimized construct map.

Retrovirus Production and Transduction of T Cells.

To produce retroviral supernatant, human embryonic kidney (HEK) 293T-cells were co-transfected with the UCAR-encoding retroviral transfer plasmid, Peg-Pam-e plasmid encoding MoMLV gag-pol, and plasmid pMEVSVg containing the sequence for VSV-G envelope, using GeneJuice transfection reagent (EMD Biosciences, San Diego, Calif.). Supernatants containing retroviral vector were collected 48 and 72 hours later.

Anti-CD3 (OKT3)/anti-CD28-activated T cells were transduced with retroviral vectors as described. Briefly, PBMCs were isolated by Lymphoprep (Bio-One, Monroe, N.C.) then activated with OKT3 (OrthoBiotech, Raritan, N.J.) and CD28 monoclonal antibodies (BD Biosciences, Palo Alto, Calif.) at a final concentration of 1 μg/mL. On day 2, recombinant human IL-2 (Chiron, Emeryville, Calif.) was added at a final concentration of 100 U/mL, and two days later, cells were harvested for retroviral transduction over recombinant fibronectin fragment (Takara-Bio-USA, Madison, Wis.) pre-coated plates. Subsequently, 3×10$^5$ T-cells per well were transduced with retrovirus in the presence of 100 U/mL IL-2. After 48-72 hours, cells were removed and expanded in the presence of 50-100 U/mL IL-2 for 10-15 days prior to use.

Flow Cytometry.

Analysis was done with a Gallios instrument (Beckman Coulter Inc, Brea, Calif.) or Accuri C6 (Becton Dickinson, Franklin Lakes, N.J.). Kaluza software (Beckman Coulter) or FlowJo data analysis software (FLOWJO, LLC, Ashland, Oreg.) was used for all flow cytometric analyses of >10,000 events; negative controls included isotype antibodies. Cells were washed with PBS containing 2% FBS and 0.1% sodium azide (FACS buffer; Sigma Aldrich, St. Louis, Mo.) before adding the antibody. After 30 to 60 minutes incubating at 4° C. in the dark, cells were washed with FACs buffer and fixed in 0.5% paraformaldehyde for analysis.

Surface staining of tumor cells was done using a goat anti-human IL13 Ra2, a mouse anti-human HER2.PE (R&D Systems, Minneapolis, Minn.), and a mouse anti-human EphA2 Alexa Fluor 488 (R&D Systems) and mouse anti-IL13Rα2.PE (R&D Systems). Cell surface expression of FRP5 was detected using goat anti-mouse Fab fragment specific antibody conjugated with Alexa Fluor 647 (Jackson ImmunoResearch, West Grove, Pa.). IL-13 mutein was detected using a goat anti-human Fc fragment specific antibody conjugated with FITC (Millipore, Billerica, Mass.).

Confocal Imaging of CAR Synapse.

For confocal microscopy, conjugates between CAR T cells and GBM cells were incubated for 45 minutes at 37° C. and then fixed and stained for IL13Rα2, HER2, and EphA2. No permeabilization step was performed for surface staining. Biotinylated HER2 affibody (Abcam, Cambridge, Mass.) and goat anti-human IL13Rα2 primary antibody (Bioss Inc., Woburn, Mass.), and a rabbit anti-human EphA2 FITC-conjugated antibody were used with appropriate secondary antibodies. Conjugates were imaged as z stacks of 0.2 micron thickness to cover the entire volume of the immunological synapse, determined individually for each conjugate, on a Zeiss Axio-Observer Z1 equipped with a Yokogawa CSU10 spinning disc, Zeiss 63× 1.43 NA objective, and Hamamatsu Orca-AG camera. Images were acquired and analyzed with Volocity software (PerkinElmer, Waltham, Mass.). All data was graphed using the GraphPad Prism software (GraphPad, La Jolla, Calif.). Statistical analysis was performed using the Student Two Tailed Unpaired T test. P>0.05 was not considered significant.

Analysis of Cytokine Production and T Cell Expansion.

T cells were co-cultured with autologous GBM or U373 cells in 1:1 (100,000 cells) ratios. After 24-hour incubation, conditioned-culture media were collected and levels of IFNγ and IL-2 were determined by ELISA as per manufacturer's instructions (R&D Systems). To assess T cell activation upon encountering immobilized target TAA, non-tissue culture treated 24-well plates (BD Falcon™, Franklin lakes, NJ) were kept overnight at 4° C. with HER2.Fc (range 0-0.8 ug/mL; R&D Systems), IL13Rα2.Fc (range 0-10 ug/mL; R&D Systems), or EphA2 Fc an irrelevant target (monoclonal anti-idiotype 1A7 and a non-specific T cell receptor stimulant (OKT3). After T cell incubation for 2 hours at 37° C., the supernatant was analyzed for IFNγ and IL-2.

Cytotoxicity Assays.

Cytolytic activity of T cells was assessed using $^{51}$Cr assays known in the art. Briefly, 1×10$^6$ target cells were labeled with 0.1 mCi (3.7 MBq) $^{51}$Cr and mixed with decreasing numbers of effector cells to give effector to target ratios of 40:1, 20:1, 10:1 and 5:1. Target cells incubated in complete medium alone or in 1% Triton X-100 were used to determine spontaneous and maximum $^{51}$Cr release, respectively. After 4 hours supernatants and measured radioactivity were collected in a gamma counter (Cobra Quantum; PerkinElmer, Wellesley, Mass.). The mean percentage of specific lysis of triplicate wells was calculated according to the following formula: [test release−spontaneous release]/[maximal release−spontaneous release]×100.

Orthotopic Xenogeneic SCID Mouse Model of GBM.

All animal experiments were conducted on a protocol approved by the Baylor College of Medicine Institutional Animal Care and Use Committee (IACUC). Recipient NOD-SCID mice were purchased from Taconic, Hudson, N.Y. (C.B-Igh-1$^b$/IcrTac-Prkdc$^{scid}$; FOX CHASE CB-17 SCID™ ICR). Male 9 to 12 week old mice were anesthetized with rapid sequence inhalation using Isofluorane (Abbot Laboratories, England) followed by intraperitoneal injection of 225-240 mg/kg Avertin® solution and maintained on Isofluorane by inhalation throughout the procedure. Mouse heads were shaved, immobilized in a Cunningham™ Mouse/Neonatal Rat Adaptor (Stoelting, Wood Dale, Ill.) stereotactic apparatus fitted into an E15600 Lab Standard Stereotaxic Instrument (Stoelting), then scrubbed with 1% povidone-iodine. A 10 mm skin incision was made along the midline. The tip of a 31G ½ inch needle mounted on a Hamilton syringe (Hamilton, Reno, Nev.) served as the reference point. A 1 mm burr-hole was drilled into the skull, 1 mm anterior to and 2 mm to the right of bregma.

U373-GBM cells were transduced with a retroviral vector encoding an eGFP. Firefly luciferase fusion gene to enable bioluminescence imaging. Cells were sorted for GFP positivity and firefly luciferase expression was confirmed in vitro prior to usage in a luminometer. Firefly-luciferase expressing U373 cells (1×10$^5$ in 2 µL) were injected 3 mm deep to bregma, corresponding to the center of right caudate nucleus over 3 minutes for 6 groups of 5 mice each. Needle was left in place for 1 minute, avoiding tumor cell extrusion, and withdrawn slowly over 3 minutes. All animals had progressively growing xenografts, evidenced by progressive and exponential increments in bioluminescence signal. Each group was randomly assigned a condition of no treatment, NT T cells, optimum uni-specific T cells, or UCAR T cells and received an intra-tumoral injection of 1×10$^6$ T cells on day 6-8 following tumor injection. T cell injections were performed following the same protocol as tumor injection. Incisions were closed with 2 to 3 interrupted 7.0 Ethicon® sutures (Ethicon Inc. Somerville, N.J.). Subcutaneous injection of 0.03-0.1 mg/kg buprenorphine (Buprenex® RBH, England) was given for pain control.

Bioluminescence Imaging.

Isofluorane anesthetized animals were imaged using the IVIS® system (Xenogen Corp, Alameda, Calif.) 10 minutes after intraperitoneal injection of 150 mg/kg D-luciferin (Xenogen, Alameda, Calif.). Photons emitted from luciferase-expressing cells within the animal body and transmitted through the tissue were quantified using "Living Image" software program (Xenogen, Alameda, Calif.). A pseudo-color image representing light intensity (blue least intense and red most intense) was generated and superimposed over the grayscale reference image. Animals were imaged every other day for one week after injections, bi-weekly for the next two weeks, and weekly thereafter until day 76. Mice were regularly examined for neurological deficits, weight loss, or signs of stress, and euthanized according to pre-set criteria by the Baylor College of Medicine's Center for Comparative Medicine guidelines.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of treating glioma in an individual, comprising the step of delivering to the individual a therapeutically effective amount of cells comprising:
    a) an expression construct that encodes a HER2-specific chimeric antigen receptor (CAR);
    b) an expression construct that encodes an IL13Rα2-specific CAR; and
    c) an expression construct that encodes an EphA2-specific CAR,
    wherein the expression constructs of a), b), and c) are located on the same molecule, wherein the cells express the HER2-specific CAR, the IL13Rα2-specific CAR, and the EphA2-specific CAR.

2. The method of claim 1, wherein the individual has a cancer that expresses HER2, IL13Rα2, and EphA2.

3. The method of claim 1, comprising the step of analyzing a sample comprising cancer cells from the individual for one or more antigens on one or more cancer cells.

4. The method of claim 3, wherein the cells comprising the composition are produced to target one or more particular antigens based on an outcome of the analyzing step.

5. The method of claim 1, wherein the expression constructs of a), b), and c) are a total of at least 4.6 kb in size.

6. The method of claim 1, wherein the expression constructs of a), b), and c) do not comprise any identical sequences greater than 50 bp in length.

7. The method of claim 1, wherein the individual was previously treated for glioma with a previous treatment.

8. The method of claim 7, wherein the individual was refractory for the previous treatment.

9. The method of claim 1, wherein the cells further comprise an expression construct that encodes an additional CAR that targets a tumor antigen that is not HER2, IL13Rα2, or EphA2, wherein the cells express the additional CAR.

* * * * *